United States Patent
Sonenfeld et al.

(10) Patent No.: US 8,172,573 B2
(45) Date of Patent: May 8, 2012

(54) METHODS AND APPARATUS FOR DENTAL IMPLANTATION

(75) Inventors: Uri Sonenfeld, Jerusalem (IL); Uri Malul, Jerusalem (IL)

(73) Assignee: Image Navigation Ltd, Moshav Ora (IL)

( * ) Notice: Subject to any disclaimer, the term of this patent is extended or adjusted under 35 U.S.C. 154(b) by 787 days.

(21) Appl. No.: 11/911,928

(22) PCT Filed: Apr. 11, 2006

(86) PCT No.: PCT/IL2006/000473
§ 371 (c)(1),
(2), (4) Date: Apr. 4, 2008

(87) PCT Pub. No.: WO2006/111964
PCT Pub. Date: Oct. 26, 2006

(65) Prior Publication Data
US 2008/0171305 A1    Jul. 17, 2008

Related U.S. Application Data

(60) Provisional application No. 60/672,615, filed on Apr. 18, 2005.

(51) Int. Cl.
*A61C 8/00* (2006.01)
(52) U.S. Cl. .......................................... 433/173; 433/75
(58) Field of Classification Search .................. 433/215, 433/72–76, 34, 37, 44, 50, 55–56, 213–214, 433/172–174
See application file for complete search history.

(56) References Cited

U.S. PATENT DOCUMENTS

| | | | |
|---|---|---|---|
| 3,514,858 A * | 6/1970 | Silverman | 433/174 |
| 4,325,373 A | 4/1982 | Slivenko et al. | |
| 5,133,660 A | 7/1992 | Fenick | |
| 5,343,391 A | 8/1994 | Mushabac | |
| 5,383,454 A | 1/1995 | Bucholz | |
| 5,688,118 A | 11/1997 | Hayka et al. | |
| 5,697,779 A | 12/1997 | Sachdeva et al. | |
| 5,770,943 A | 6/1998 | Zhou | |
| 5,842,858 A | 12/1998 | Truppe | |
| 5,856,844 A | 1/1999 | Batterman et al. | |
| 5,859,922 A | 1/1999 | Hoffmann | |
| 5,867,696 A | 2/1999 | Okayama et al. | |
| 5,872,829 A | 2/1999 | Wischmann et al. | |
| 5,885,077 A * | 3/1999 | Jeffer | 433/168.1 |
| 5,927,982 A | 7/1999 | Kruger | |
| 5,967,777 A | 10/1999 | Klein et al. | |

(Continued)

FOREIGN PATENT DOCUMENTS

DE    19615456    10/1997

(Continued)

*Primary Examiner* — Cris L Rodriguez
*Assistant Examiner* — Hao D Mai
(74) *Attorney, Agent, or Firm* — Mark M. Friedman

(57) ABSTRACT

A method for implanting a tooth implant in an at least partially edentulous patient including the steps of anchoring at least one attachment element in a patient's jaw bone, removeably and replaceably mounting a carrier assembly bearing at least one fiducial marker onto the at least one attachment element in a precisely repeatable position with respect to the patient's jaw bone, employing the carrier assembly for providing registration between the at least one fiducial marker and the patient's jaw bone and implanting the tooth implant by employing a tracking system which uses the registration to guide a drilling assembly.

33 Claims, 25 Drawing Sheets

U.S. PATENT DOCUMENTS

| | | |
|---|---|---|
| 5,993,211 A | 11/1999 | Broberg et al. |
| 6,076,008 A | 6/2000 | Bucholz |
| 6,228,089 B1 | 5/2001 | Wahrburg |
| 6,236,875 B1 | 5/2001 | Bucholz et al. |
| 6,315,555 B1 | 11/2001 | Bortolotti et al. |
| 6,340,367 B1 | 1/2002 | Stinson et al. |
| 6,382,977 B1 | 5/2002 | Kumar |
| 6,402,707 B1 | 6/2002 | Ernst et al. |
| 6,434,507 B1 | 8/2002 | Clayton et al. |
| 6,447,296 B2 | 9/2002 | Worthington |
| 6,497,134 B1 | 12/2002 | Faul et al. |
| 6,640,128 B2 | 10/2003 | Vilsmeier et al. |
| 6,814,575 B2 | 11/2004 | Poirier et al. |
| 6,902,401 B2 | 6/2005 | Jorneus et al. |
| 6,905,336 B2 | 6/2005 | Summers |
| 6,932,823 B2 | 8/2005 | Grimm et al. |
| 7,006,085 B1 | 2/2006 | Acosta et al. |
| 7,457,443 B2 | 11/2008 | Persky |
| 7,653,455 B2 * | 1/2010 | Cinader, Jr. .................. 700/119 |
| 7,785,108 B2 * | 8/2010 | Tache et al. .................. 433/173 |

FOREIGN PATENT DOCUMENTS

| | | |
|---|---|---|
| DE | 19750637 | 7/1998 |
| EP | 0488987 | 6/1992 |
| WO | WO-9956156 | 11/1999 |
| WO | 02096261 | 12/2002 |

* cited by examiner

FIG. 1D
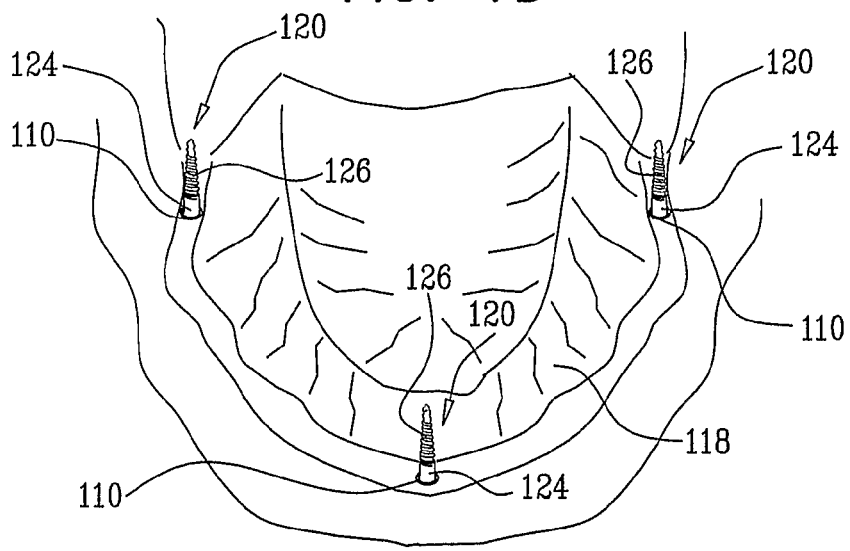
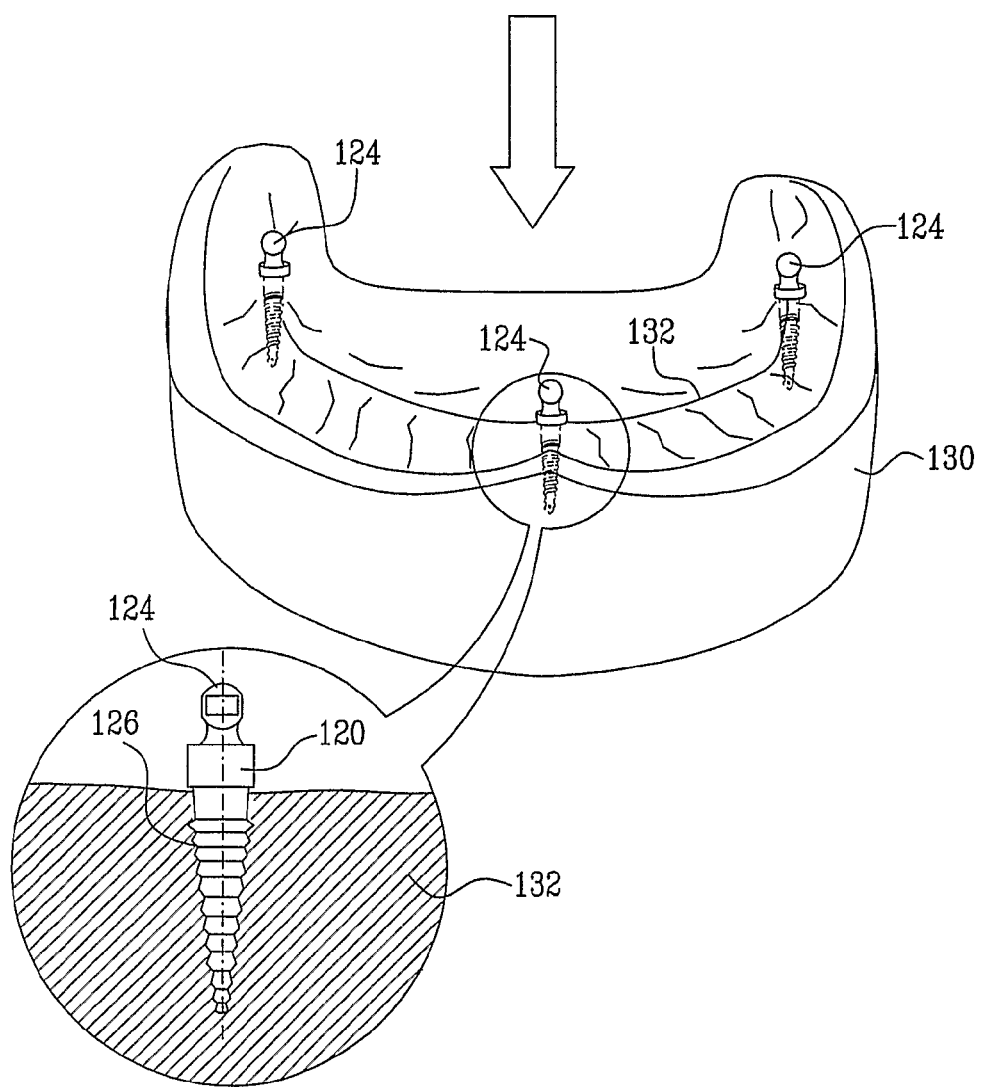

FIG. 1H
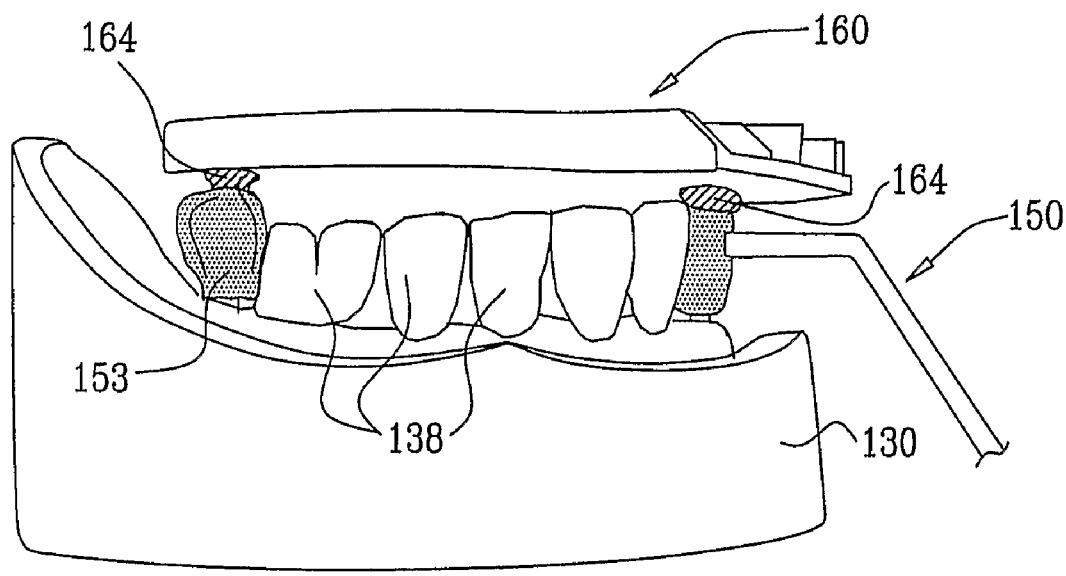
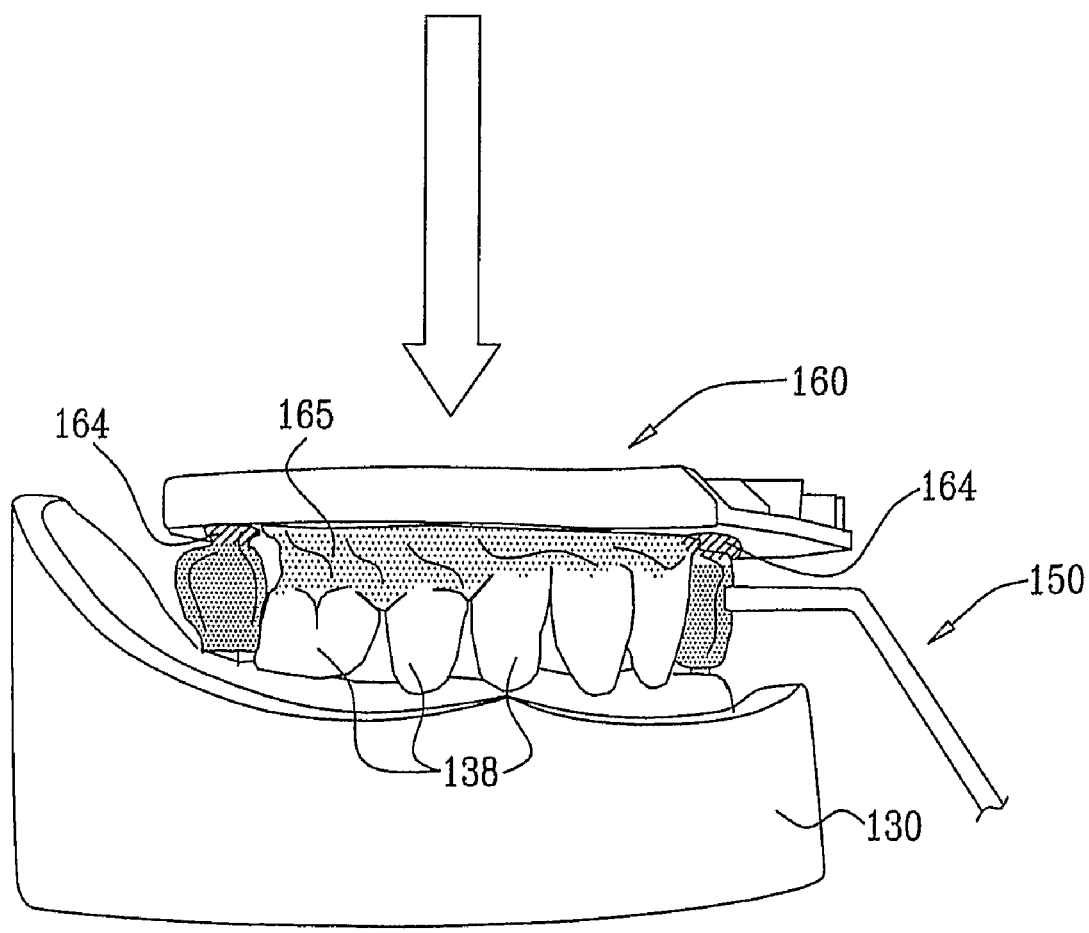

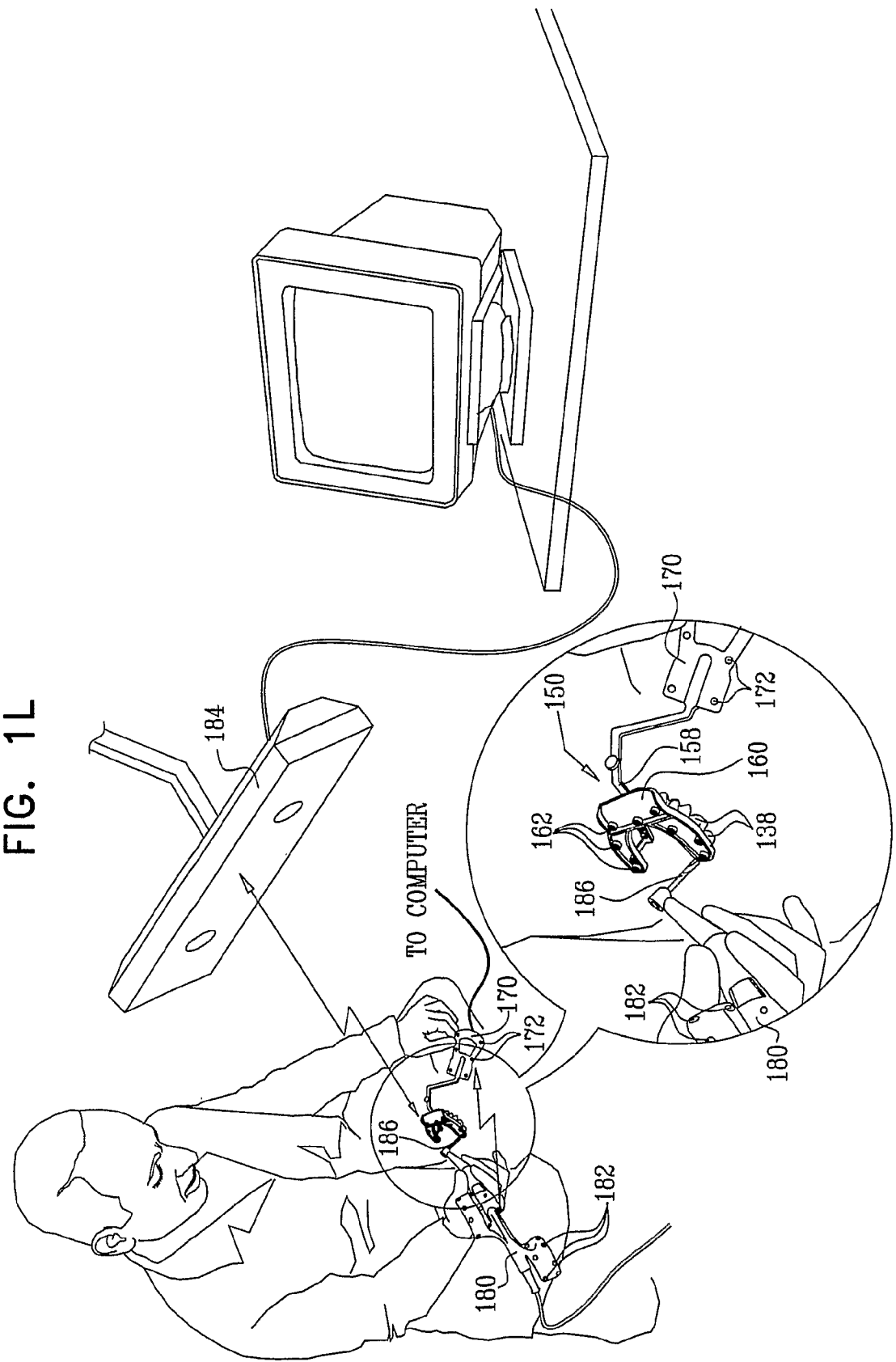

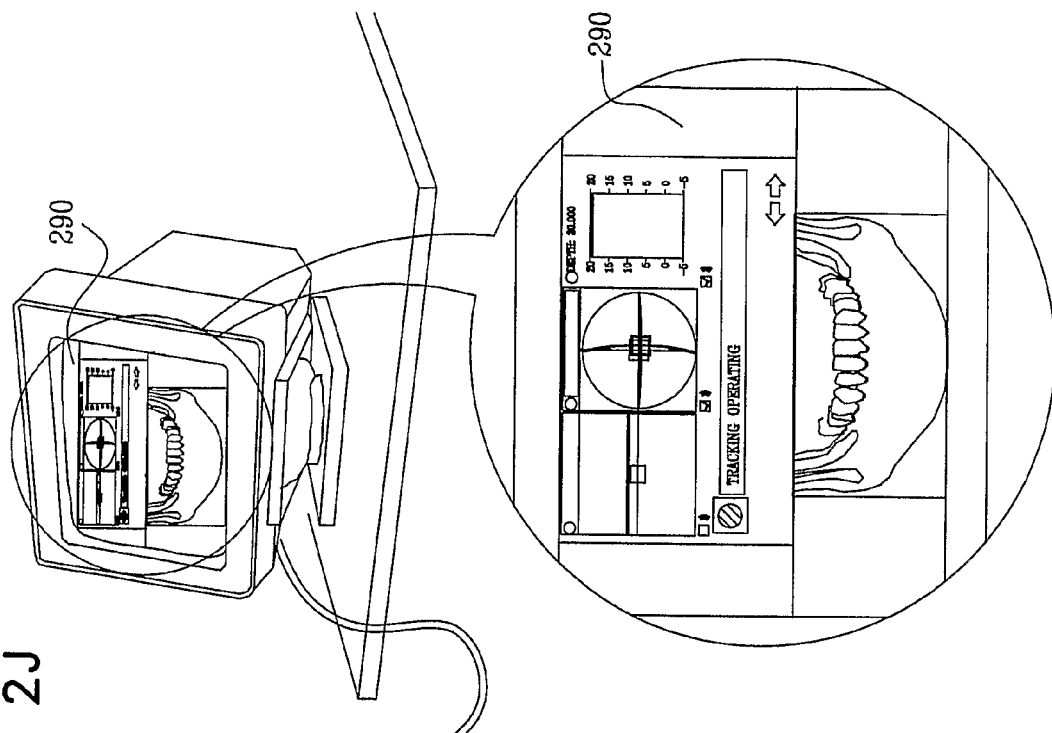
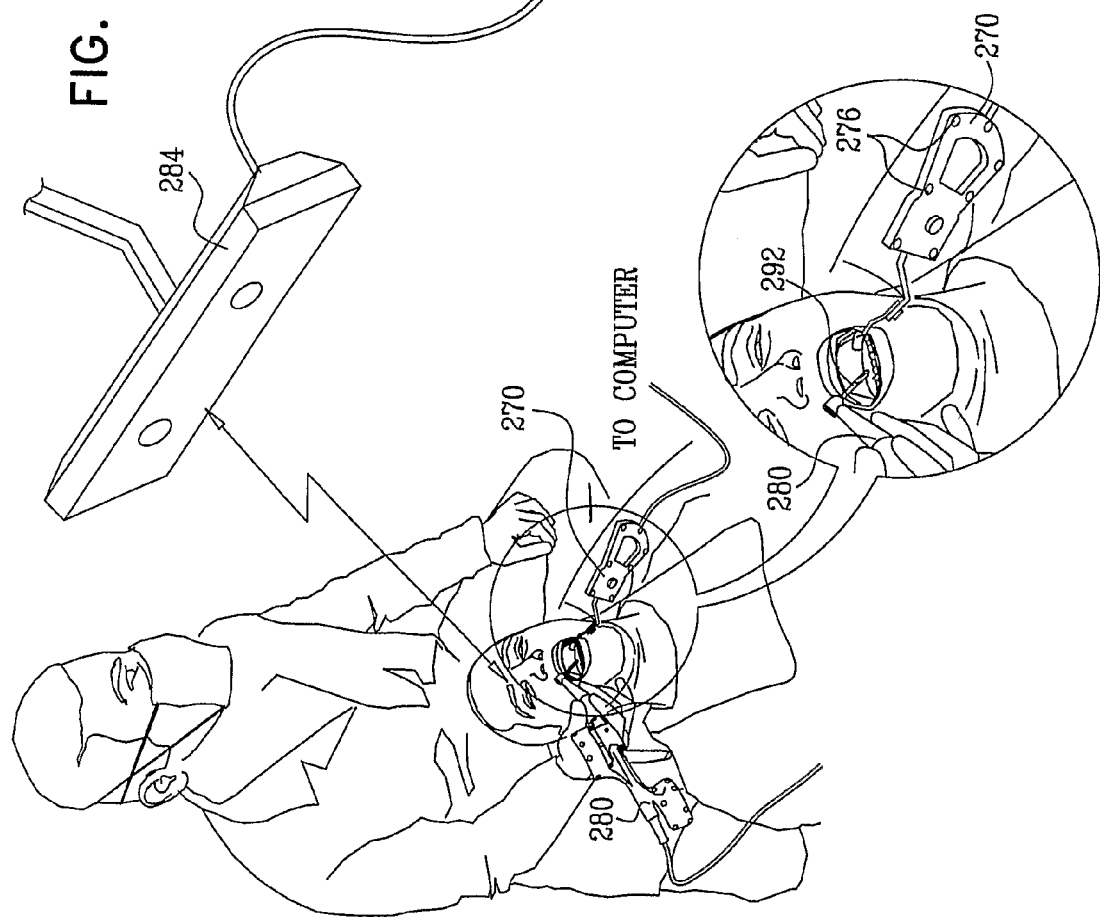
FIG. 2J

METHODS AND APPARATUS FOR DENTAL IMPLANTATION

REFERENCE TO RELATED APPLICATIONS

This application is the U.S. national phase of International Application No. PCT/IL2006/000473, filed Apr. 11, 2006, which claims priority from U.S. Provisional Patent Application No. 60/672,615, entitled IGI EDENTULOUS PATIENT KIT, filed Apr. 18, 2005 and to U.S. Provisional Patent Application No. 60/733,197, entitled ACCURATE REPEATABLE BITE SPLINT, filed Nov. 4, 2005, the disclosures of which are hereby incorporated by reference and priority of which is hereby claimed pursuant to 37 CFR 1.78(a)(4) and (5)(i). The International Application published in English on Oct. 26, 2006 as WO 2006/111964 under PCT Article 21(2).

Reference is made to U.S. Provisional Patent Application No. 60/672,615, entitled IGI EDENTULOUS PATIENT KIT, filed Apr. 18, 2005, and to U.S. Provisional Patent Application No. 60/733,197, entitled ACCURATE REPEATABLE BITE SPLINT, filed Nov. 4, 2005, the disclosures of which are hereby incorporated by reference and priority of which is hereby claimed pursuant to 37 CFR 1.78(a) (4) and (5)(i).

FIELD OF THE INVENTION

The present invention relates to methods and apparatus for dental implantation.

BACKGROUND OF THE INVENTION

The following patent documents, the disclosures of which are hereby incorporated by reference, are believed to represent the current state of the art:

U.S. Pat. Nos. 6,902,401; 6,814,575; 6,382,977; 6,315,555; 5,927,982; 6,905,336; 5,993,211; 6,447,296; 6,640,128; 6,932,823; 6,497,134; 5,856,844; 6,402,707; 6,340,367; 5,867,696; 5,697,779; 7,006,085 and 6,434,507; and Applicant/Assignee's Published PCT Application No. WO02/096261.

SUMMARY OF THE INVENTION

The present invention seeks to provide an improved apparatus and methods for operating on partially or fully edentulous patients.

There is thus provided in accordance with a preferred embodiment of the present invention a method for implanting a tooth implant in an at least partially edentulous patient including the steps of anchoring at least one attachment element in a patient's jaw bone, removably and replaceably mounting a carrier assembly bearing at least one fiducial marker onto the at least one attachment element in a precisely repeatable position with respect to the patient's jaw bone, employing the carrier assembly for providing registration between the at least one fiducial marker and the patient's jaw bone and implanting the tooth implant by employing a tracking system which uses the registration to guide a drilling assembly.

In accordance with a preferred embodiment of the present invention the at least one attachment element includes at least one jaw bone fastener. Preferably, the at least one attachment element includes three jaw bone fasteners each having a generally ball-shaped head. Additionally or alternatively, the jaw bone fasteners are bone screws.

In accordance with another preferred embodiment of the present invention the method also includes, following the anchoring and prior to the removably and replaceably mounting a carrier assembly, removeably and replaceably mounting at least one intermediate element on the at least one attachment element, taking an impression of the patient's jaw, employing the impression of the patient's jaw to provide a model of the patient's jaw, mounting at least one carrier mount onto the at least one intermediate element and mounting a fiducial carrier bearing the at least one fiducial marker onto the at least one carrier mount, thereby to provide the carrier assembly. Preferably, the removably and replaceably mounting at least one intermediate element includes removably and replaceably mounting at least one impression cap having a flat surface onto the at least one attachment element. Additionally or alternatively, the removably and replaceably mounting at least one intermediate element includes removably and replaceably mounting three impression caps, each having a flat surface onto each of the generally ball shaped heads.

In accordance with yet another preferred embodiment of the present invention the method also includes, prior to the anchoring, taking a preliminary impression of the patient's jaw and employing the preliminary impression for preparing a temporary base and rim suited to the patient's jaw. Preferably, the taking an impression includes employing the temporary base and rim as an impression tray while taking the impression. Additionally and preferably, the taking an impression includes taking an impression which has the at least one intermediate element adhered thereto.

In accordance with still another preferred embodiment of the present invention the employing the impression of the patient's jaw to provide a model includes employing the impression to provide the model, which has anchored therein at least one attachment element analog, removeably positioning radio-opaque artificial teeth on the model. Preferably, the removeably positioning radio-opaque artificial teeth includes removeably positioning radio-opaque artificial teeth on the model while the model is in an articulator. Additionally or alternatively, the mounting at least one carrier mount onto the at least one intermediate element includes adhering the at least one carrier mount to the at least one intermediate element, while the at least one intermediate element is mounted onto the at least one attachment element analog.

In accordance with a further preferred embodiment of the present invention the mounting a fiducial carrier includes employing a first adhesive to adhere the fiducial carrier to the at least one carrier mount. Preferably, the mounting a fiducial carrier includes employing a second adhesive to adhere the fiducial carrier to the radio-opaque artificial teeth. Additionally or alternatively, the removably and replaceably mounting a carrier assembly includes removably and replaceably mounting the at least one intermediate element, the at least one carrier mount, the radio-opaque artificial teeth and the fiducial carrier onto the at least one attachment element in a precisely repeatable position with respect to the patient's jaw bone.

In accordance with yet a further preferred embodiment of the present invention the employing the carrier assembly for providing registration includes providing at least one CT image of the patient's jaw while the carrier assembly is mounted onto the at least one attachment element. Preferably, the method also includes, prior to the implanting the tooth implant providing three-dimensional registration between the at least one fiducial marker, the tracking system and the drilling assembly. Additionally or alternatively, the method also includes, prior to the implanting the tooth implant and following the employing the carrier assembly for providing registration, removing the radio-opaque artificial teeth and the fiducial carrier from the carrier assembly.

In accordance with still a further preferred embodiment of the present invention the removing includes employing a cutting device to cut the first adhesive and the second adhesive.

There is also provided in accordance with a preferred embodiment of the present invention apparatus for use in implanting a tooth implant including at least one attachment element including an anchor portion configured for anchoring in a patient's jaw bone and an attachment portion and a fiducial marker carrier assembly containing a plurality of fiducial markers and including at least one mounting portion configured for removable and replaceable mounting onto the attachment portion of the at least one attachment element in a precisely repeatable position with respect to the patient's jaw bone.

In accordance with a preferred embodiment of the present invention the at least one attachment element includes at least one jaw bone fastener. Preferably, the at least one jaw bone fastener includes three jaw bone fasteners, each having a generally ball-shaped head and the at least one mounting portion includes three mounting portions, each configured for removable and replaceable mounting onto the attachment portion of one of the three jaw bone fasteners in a precisely repeatable position with respect to the patient's jaw bone. Additionally or alternatively, the jaw bone fasteners are bone screws.

In accordance with another preferred embodiment of the present invention the apparatus also includes at least one intermediate element configured to be mounted onto the attachment portion of the at least one attachment element and to have the fiducial marker carrier assembly mounted thereon, at least one carrier mount configured to be mounted onto the at least one intermediate element and a fiducial carrier bearing the plurality of fiducial markers configured to be mounted onto the at least one carrier mount, thereby to provide the fiducial marker carrier assembly. Preferably, the at least one intermediate element includes at least one impression cap having a flat surface. Additionally or alternatively, the fiducial marker carrier assembly includes the at least one intermediate element, the at least one carrier mount, the fiducial carrier and a plurality of radio-opaque artificial teeth.

In accordance with still another preferred embodiment of the present invention the fiducial marker carrier assembly includes a first adhesive adhering the fiducial carrier to the at least one carrier mount and a second adhesive adhering the plurality of radio-opaque artificial teeth to the fiducial carrier. Preferably, the apparatus also includes a tracking system including at least one IR emitter configured for providing tracking of motions of a patient during implantation of the tooth implant. Additionally or alternatively, the apparatus also includes a dental surgery device including at least one IR emitter configured for providing tracking of motions of a dental surgeon during implantation of the tooth implant.

There is also provided in accordance with an additional preferred embodiment of the present invention a method for implanting a tooth implant in a patient including the steps of attaching at least one attachment element to a patient's teeth by exclusively chair-side configuring of at least a portion of the at least one attachment element to match the patient's teeth, mounting a carrier bearing at least one fiducial marker onto the at least one attachment element, employing the carrier for providing registration between the at least one fiducial marker and the patient's jaw bone and implanting the tooth implant by employing a tracking system which uses the registration to guide a drilling assembly.

In accordance with a preferred embodiment of the present invention the exclusively chair-side configuring includes molding and hardening to a rigid state of a precise tooth shape retaining material. Preferably, the attaching at least one attachment element includes fixedly attaching the at least one attachment element and the method also includes destroying the at least a portion of the at least at least one attachment element following the implanting, in order to remove the at least one attachment element from the patient's teeth. Additionally or alternatively, the attaching at least one attachment element includes removably and replaceably attaching the at least one attachment element to the patient's teeth at a precisely repeatable position with respect to the patient's jaw bone.

In accordance with another preferred embodiment of the present invention the employing the carrier for providing registration between the at least one fiducial marker and the patient's jaw bone includes providing at least one CT image of the patient's jaw while the at least one attachment element is attached to the patient's teeth and the at least one fiducial marker is mounted onto the at least one attachment element. Preferably, the method also includes prior to the implanting the tooth implant, providing three-dimensional registration between the at least one fiducial marker, the tracking system and the drilling assembly. Additionally or alternatively, the method also includes, prior to the implanting the tooth implant, removing the carrier from the at least one attachment element.

There is further provided in accordance with a further preferred embodiment of the present invention apparatus for implanting a tooth implant in a patient including a material useful for exclusively chair-side configuring of at least a portion of at least one attachment element to match the patient's teeth, a carrier assembly arranged for mounting onto the at least one attachment element and bearing at least one fiducial marker useful for providing registration between the at least one fiducial marker and the patient's jaw bone which is employed by a tracking system to guide an implant drilling assembly.

In accordance with a preferred embodiment of the present invention the material useful for exclusively chair-side configuring includes a precise tooth shape retaining material suitable for molding and hardening to a rigid state. Preferably, the at least one attachment element includes a fixedly attachable attachment element configured to be fixedly attached to the patient's teeth. Additionally or alternatively, the at least one attachment element is configured to be removably and replaceably attachable to the patient's teeth at a precisely repeatable position with respect to the patient's jaw bone.

In accordance with another preferred embodiment of the present invention the apparatus also includes a tracking system including at least one IR emitter configured for providing tracking of motions of the patient during implantation of the tooth implant. Preferably, the apparatus also includes a dental surgery device including at least one IR emitter configured for providing tracking of motions of a dental surgeon during implantation of the tooth implant.

There is also provided in accordance with another preferred embodiment of the present invention a method for implanting a tooth implant in a patient including the steps of exclusively chair-side attaching at least one radio-opaque tooth shape representation element to a patient's jaw, mounting a carrier bearing at least one fiducial marker onto the patient's jaw, employing the carrier and the at least one radio-opaque tooth shape representation element for providing registration between the at least one fiducial marker, the at least one radio-opaque tooth shape representation element and the patient's jaw bone and implanting the tooth implant by employing a tracking system which uses the registration to guide a drilling assembly.

In accordance with a preferred embodiment of the present invention the at least one radio-opaque tooth shape representation element represents a tooth which is to be replaced by the tooth implant. Alternatively the at least one radio-opaque tooth shape representation element represents a tooth opposed to a tooth which is to be replaced by the tooth implant. Preferably, the exclusively chair-side attaching includes the steps of placing a radiolucent hardenable molding material on the patient's jaw at a location of an intended tooth implant, causing the patient to bite down on the hardenable molding material to create an impression of at least one tooth opposed to a tooth which is to be replaced by the tooth implant and employing the impression, in vivo, to mold a radio-opaque material into the at least one radio-opaque tooth shape representation element.

BRIEF DESCRIPTION OF THE DRAWINGS

The present invention will be understood and appreciated more fully from the following detailed description, taken in conjunction with the drawings in which:

FIGS. 1A, 1B, 1C, 1D, 1E, 1F, 1G, 1H, 1I, 1J, 1K, 1L, 1M, 1N and 1O are simplified pictorial illustrations of various stages in a method of placing an implant on a fully edentulous patient in accordance with a preferred embodiment of the present invention; and FIGS. 2A, 2B, 2C, 2D, 2E, 2F, 2G, 2H, 2I and 2J are simplified pictorial illustrations of various stages in a method of placing an implant on a partially edentulous patient in accordance with another preferred embodiment of the present invention.

DETAILED DESCRIPTION OF PREFERRED EMBODIMENTS

Figure 1A:
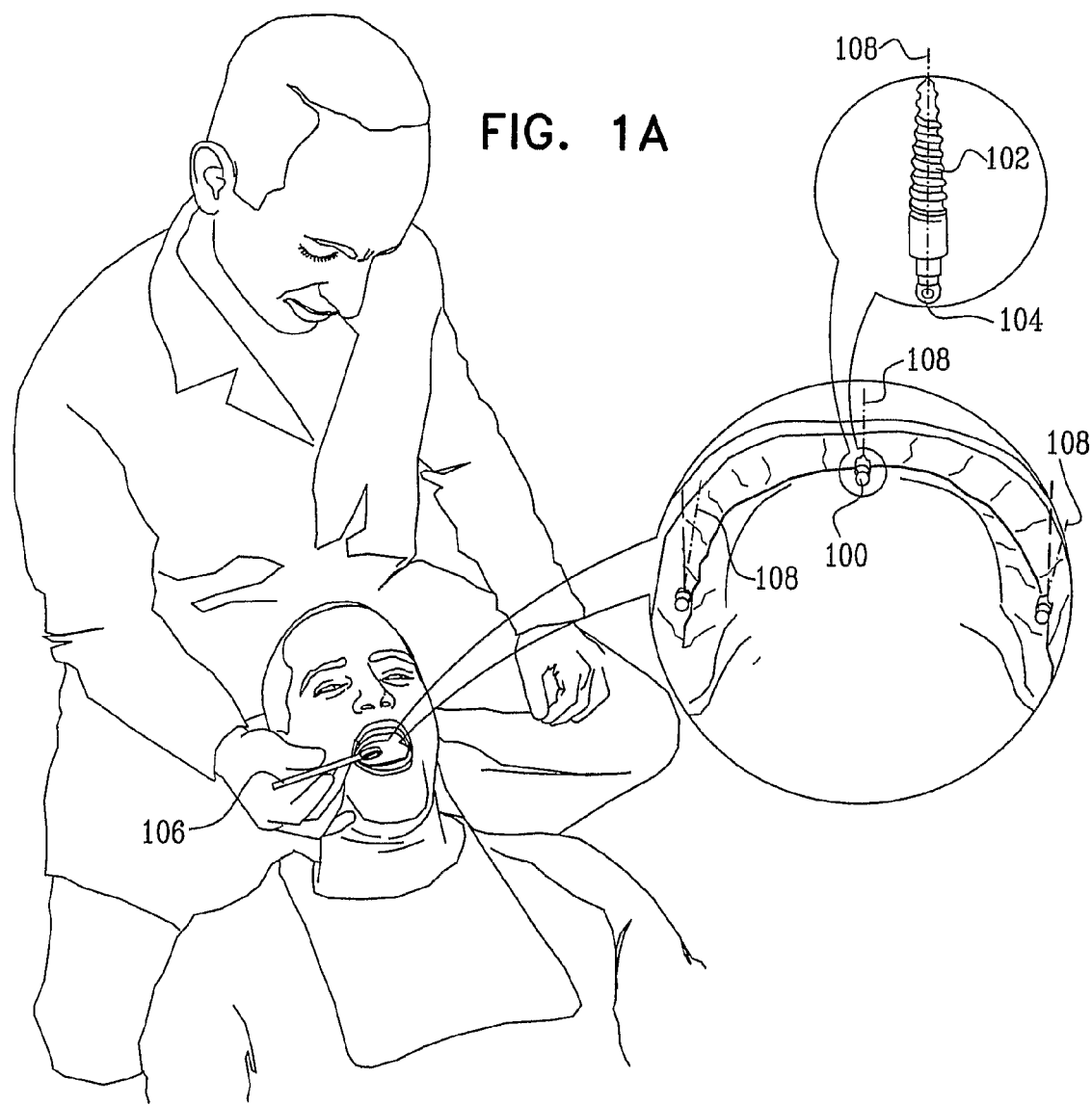

Reference is now made to FIGS. 1A, 1B, 1C, 1D, 1E, 1F, 1G, 1H, 1I, 1J, 1K, 1L, 1M, 1N and 1O, which are simplified pictorial illustrations of various stages in a method of placing an implant on an at least partially edentulous patient in accordance with a preferred embodiment of the present invention. FIGS. 1A-1O describe a method for placing a tooth implant in an at least partially edentulous patient including the steps of anchoring at least one attachment element in a patient's jaw bone, removably and replaceably mounting a carrier bearing at least one fiducial marker onto the at least one attachment element in a precisely repeatable position with respect to the patient's jaw bone, employing the carrier for providing registration between the at least one fiducial marker and the patient's jaw bone and placing the tooth implant by employing a tracking system which uses the registration to guide a drilling assembly.

Prior to the stage illustrated in FIG. 1A, a conventional impression is taken of the patient's jaw. The impression is employed conventionally in a dental laboratory to create a conventional temporary base and rim matching the patient's jaw. The temporary base and rim is employed in the invention, as described hereinbelow.

Referring now specifically to FIG. 1A, it is seen that the dentist has inserted at least one, preferably three attachment elements, each preferably including an anchor portion and an attachment portion, in a patient's jaw bone. In the illustrated embodiment of FIGS. 1A-1O, the attachment elements are preferably bone screws 100 which include a tapered, threaded screw portion 102 and a spherical head 104. Preferably, the bone screws 100 are inserted by drilling into the patient's jaw bone to a depth of approximately one-half of the length of screw portion 102 and then screwing in the bone screws 100, typically by the use of a ratchet wrench 106.

It is appreciated that due to the provision of the spherical head 104, the longitudinal axes of the bone screws 100, here designated by reference numeral 108, need not necessarily be parallel, although it is desirable that they be as parallel to each other as possible. It is preferred that the distribution of the bone screws 100 be generally as illustrated, with a center bone screw 100 preferably being located at the midline of the jaw and two additional bone screws 100 being located posterior to the most posterior of the implants to be placed.

Figure 1B:
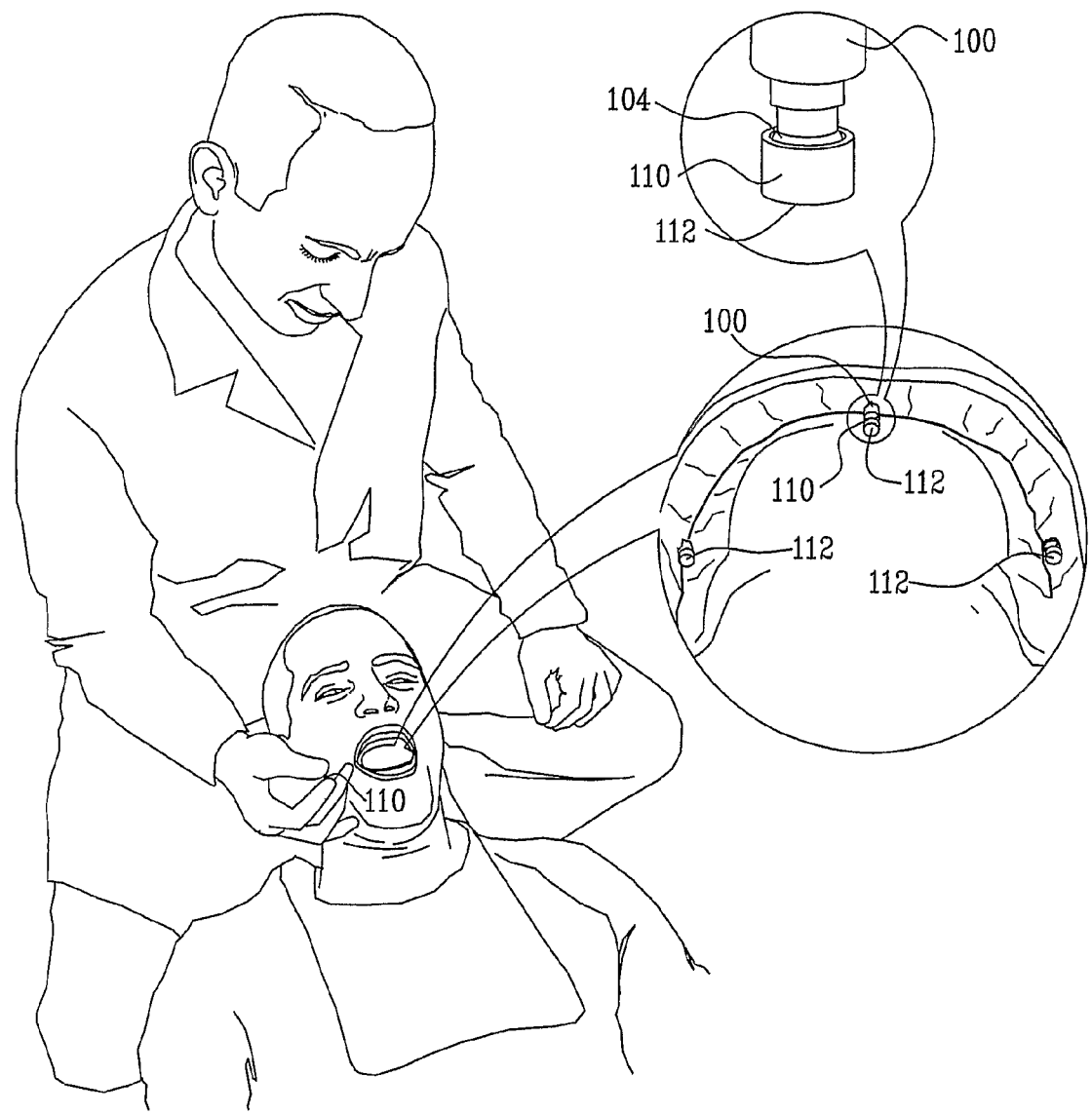

As seen in FIG. 1B, impression caps 110 are preferably removably placed onto the spherical heads 104 of the bone screws 100, preferably by snap-fit engagement therewith. The positioning of the impression caps 110 on the spherical heads 104 is preferably such that top surfaces 112 thereof all lie in a common plane.

Figure 1C:
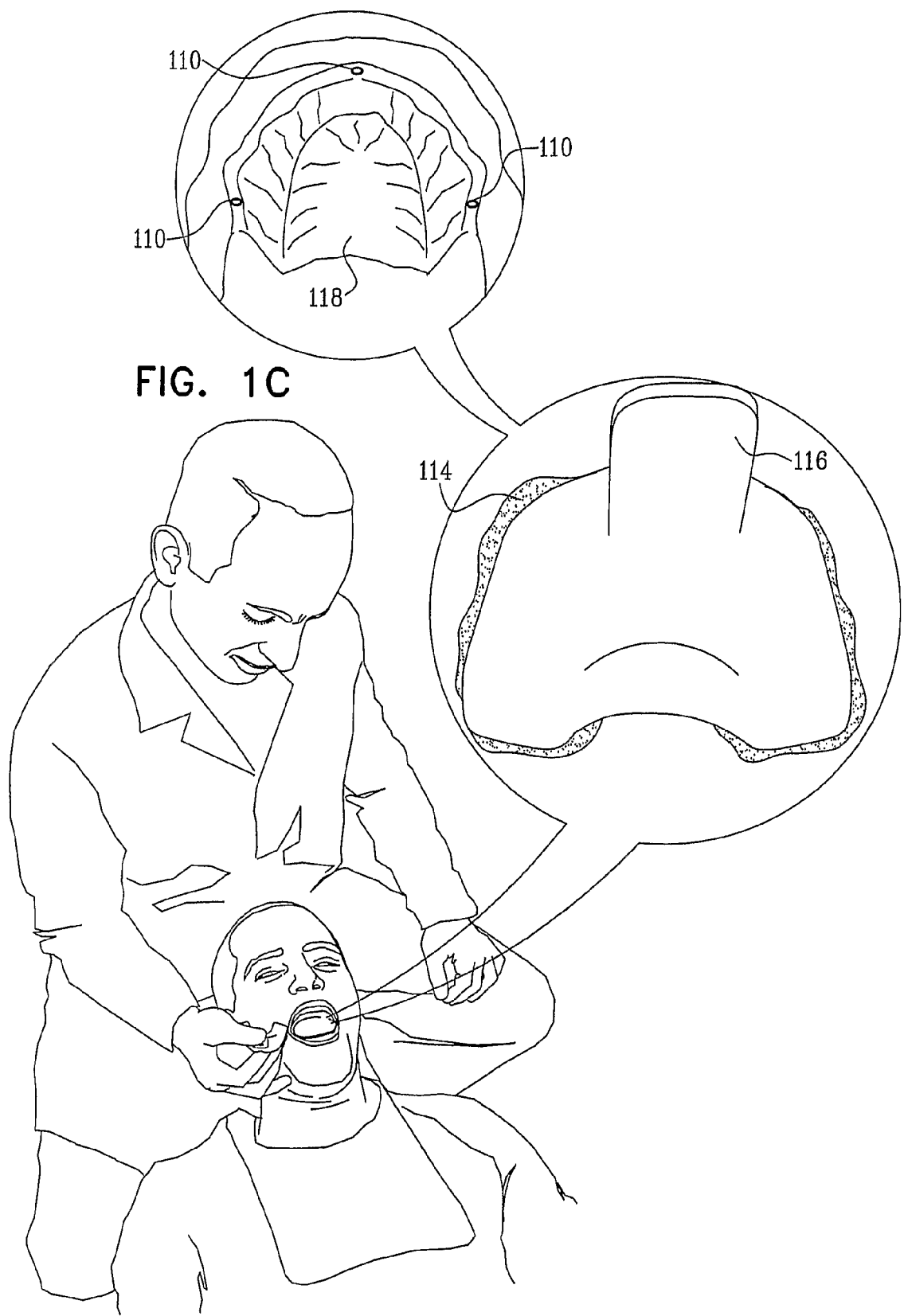

Referring now to FIG. 1C, it is seen that an impression is taken of the patient's jaw, having the impression caps 110 in place therein. The apparatus and methodology for taking the impression may be entirely conventional and may include conventional impression material 114, such as IMPREGUM SE, commercially available from 3M, and the temporary base and rim earlier prepared for the patient, which is employed as a custom tray 116.

It is noted that preferably the impression caps 110 adhere to the impression material 114 and thus form part of the impression, which is designated by reference numeral 118.

Preferably, following the step shown in FIG. 1C, bite registration is carried out in a conventional manner.

At this stage, a conventional impression preferably is taken of the antagonist jaw.

Referring now to FIG. 1D, it is seen that impression 118 is fitted with screw analogs 120 in an orientation as shown. The screw analogs 120 preferably include a spherical head analog 124, which is identical to spherical head 104 as well as a stem 126. The spherical head analogs 124 preferably snap-fit into impression caps 110, as shown. The impression 118, together with screw analogs 120, preferably is poured with plaster to form a model 130 of the patient's jaw wherein the spherical head analogs 124 protrude from the alveolar crest portion 132 of model 130 and the stems 126 are embedded in the model 130.

Figure 1E:
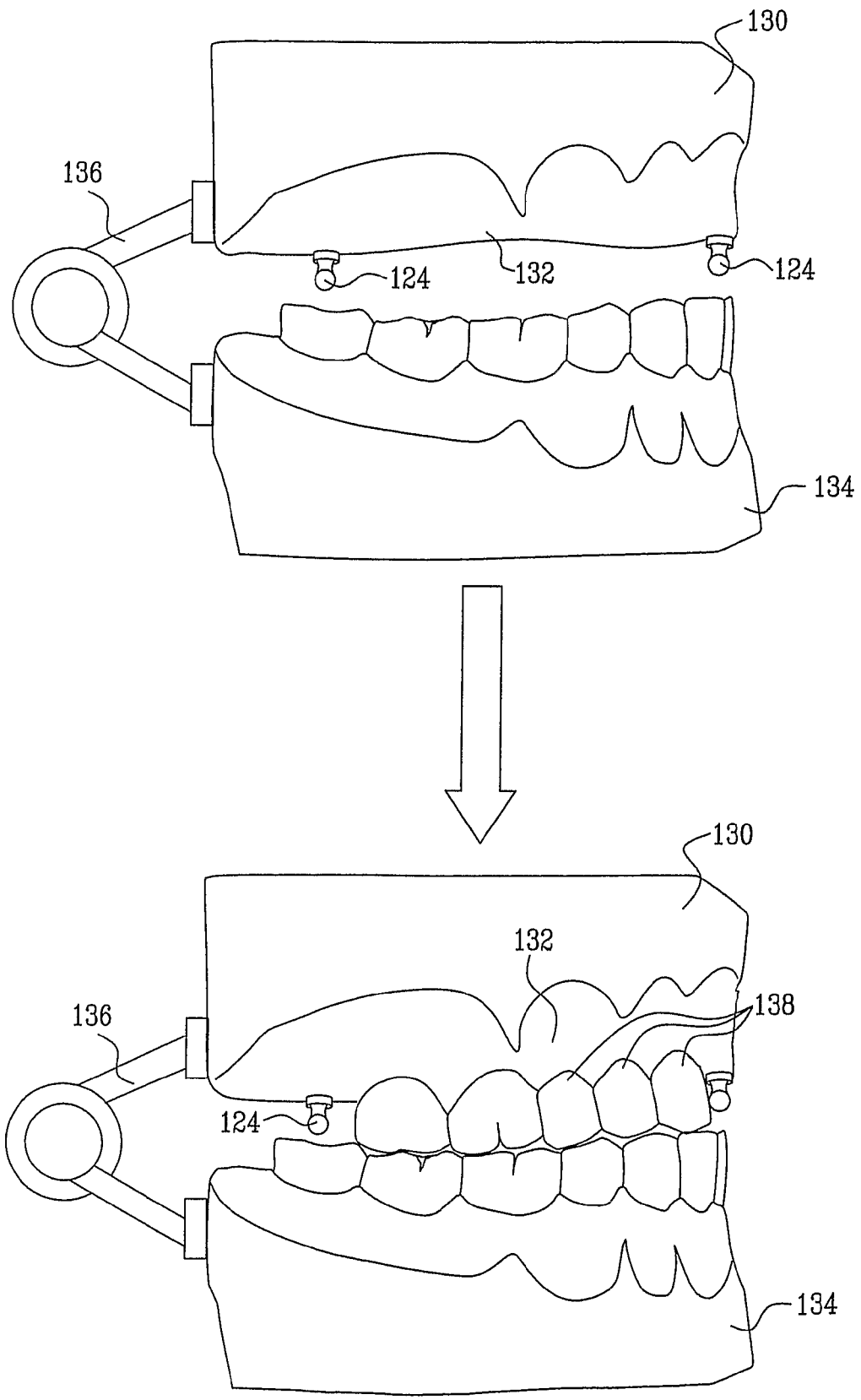

Referring now to FIG. 1E, at this stage model 130 and a conventional model 134 of the antagonist jaw are placed in an articulator 136 and radio-opaque artificial teeth 138 are removably positioned on alveolar crest portion 132 of model 130.

Figure 1F:
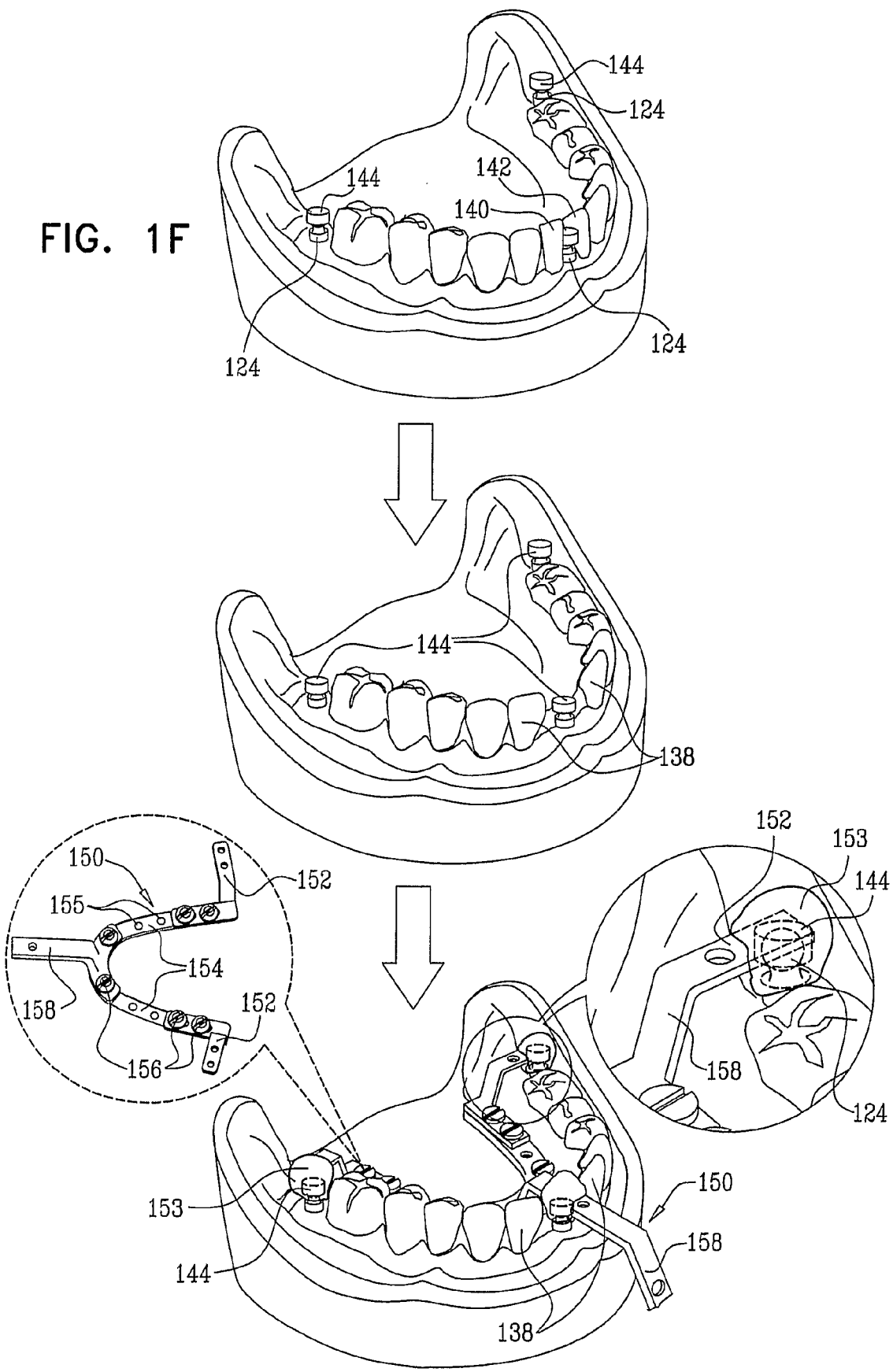

Turning to FIG. 1F, it is seen that the radio-opaque teeth, here designated by reference numeral 140 and 142, which are adjacent the spherical head analog 124 positioned along the mid line of the jaw, are removed, retentive caps 144 are snap fitted onto spherical head analogs 124 and a mounting portion 150 forming part of a fiducial marker carrier assembly (not shown) is fitted such that apertured spherical head engagement portions 152 thereof are placed over corresponding retentive caps 144, as shown. An adhesive 153, preferably pattern resin, commercially available from GC America Inc. of Alsip, Ill., USA, is placed over each apertured spherical head engagement portion 152 and corresponding retentive cap 144, in order to fixedly attach the mounting portion 150 to the retentive caps 144, such that the mounting portion 150 is securely removeably mounted in place on the spherical head analogs 124.

Preferably, as seen in FIG. 1F, the mounting portion 150 is formed of a mounting element 154 which includes a plurality of bores 155 configured for is selectable positioning with respect to apertured spherical head engagement portion 152 which are typically removably fixed thereto by screws 156, in order to enhance ease of fitting the mounting portion 150 to the jaw of a patient and to the attachment elements inserted therein. The mounting portion 150 preferably also includes a tracking device mounting rod 158.

Figure 1G:
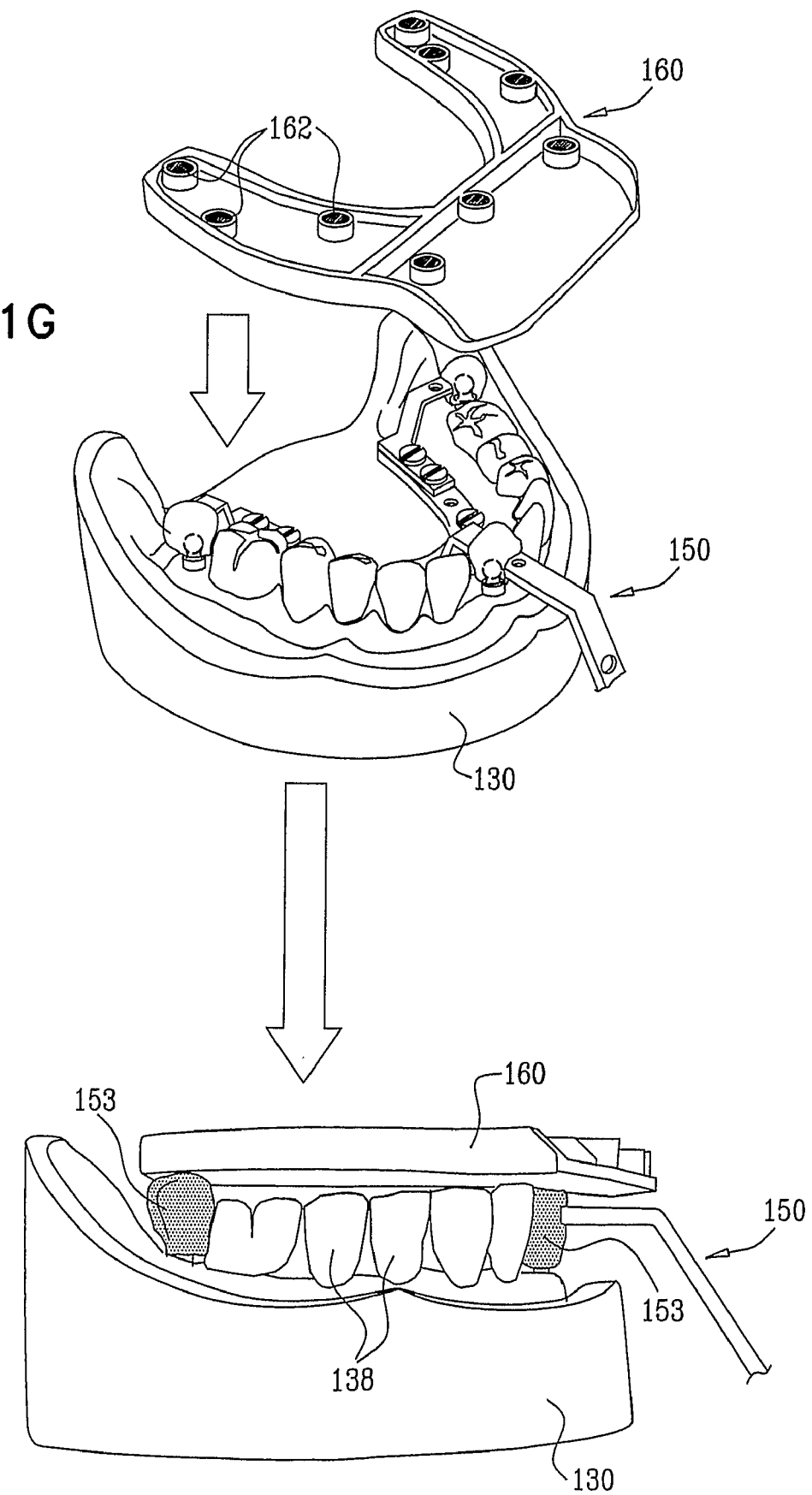

Reference is now made to FIG. 1G, which shows placement of a fiducial carrier portion 160 of the fiducial marker carrier assembly (not shown) onto the mounting portion 150 while the mounting portion 150 remains attached to the model 130. The fiducial carrier portion 160 is commercially available from Denx Ltd. of Jerusalem, Israel, under catalog number AIG 3110. A plurality of fiducial markers 162, preferably nine in number and in the form of a ceramic sphere having a diameter of 3 mm are mounted on the carrier portion 160 at precise locations thereat.

Referring now to FIG. 1H, it is seen that carrier portion 160 is adhesively fixed to mounting portion 150, preferably adjacent apertured spherical head engagement portions 152 by additional application thereat of an adhesive 164, preferably pattern resin, commercially available from GC America Inc. of Alsip, Ill., USA. Thereafter, the carrier portion 160 is adhered to the radio-opaque artificial teeth 138 by means an adhesive 165, preferably UNIFAST TRAD, commercially available from GC America Inc. of Alsip, Ill., USA.

Figure 1I:
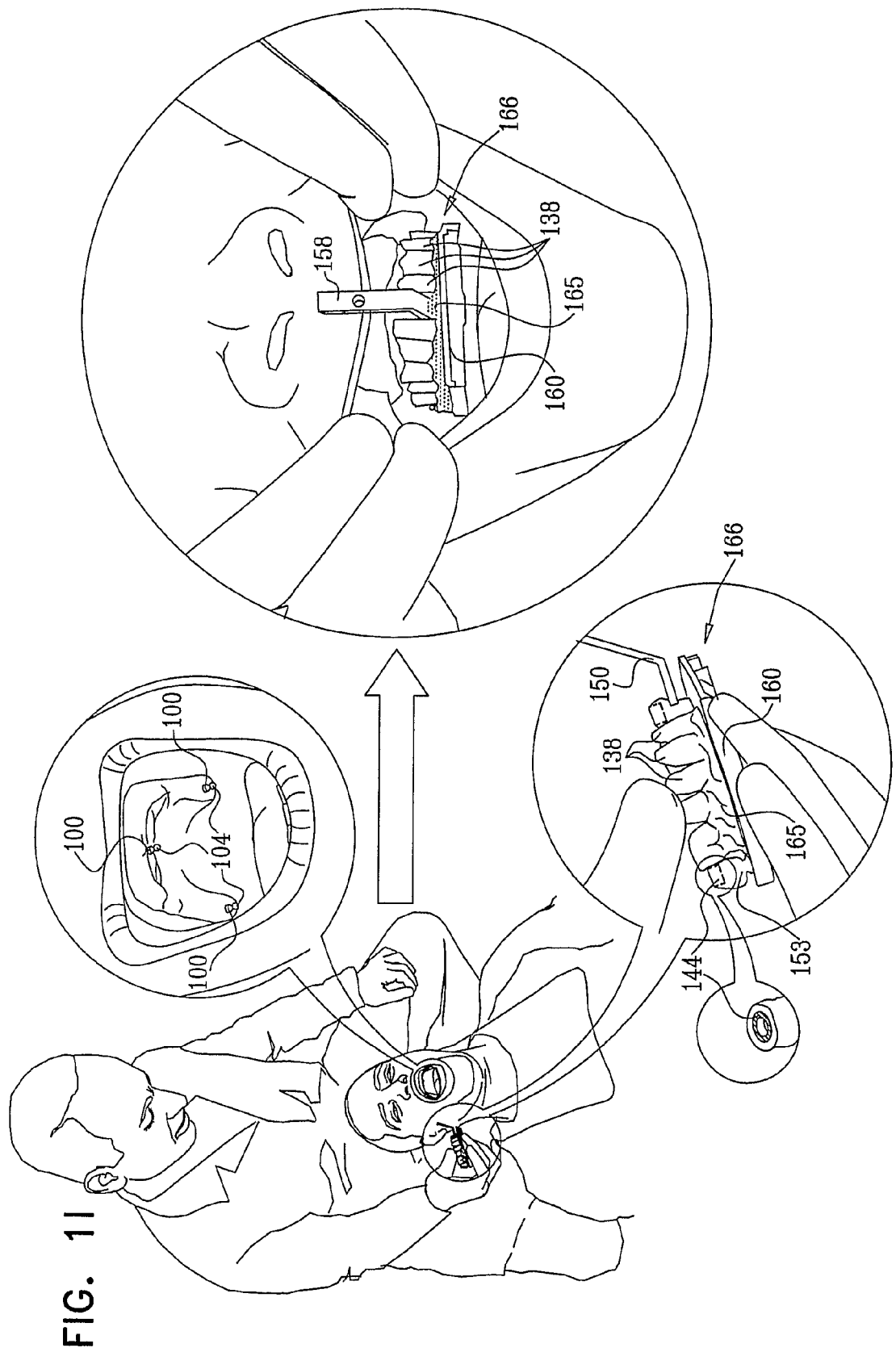

Reference is now made to FIG. 1I, which shows a CT imagable registration assembly 166, including the adhesively adhered mounting portion 150 together with retentive caps 144, carrier portion 160 and radio-opaque artificial teeth 138 having been removed from model 130 and being inserted into a patient's mouth. The assembly 166 is secured in the patient's mouth by snap fitting the retentive caps 144, fixed by adhesive 153 to mounting portion 150, onto spherical heads 104 of bone screws 100.

Figure 1J:
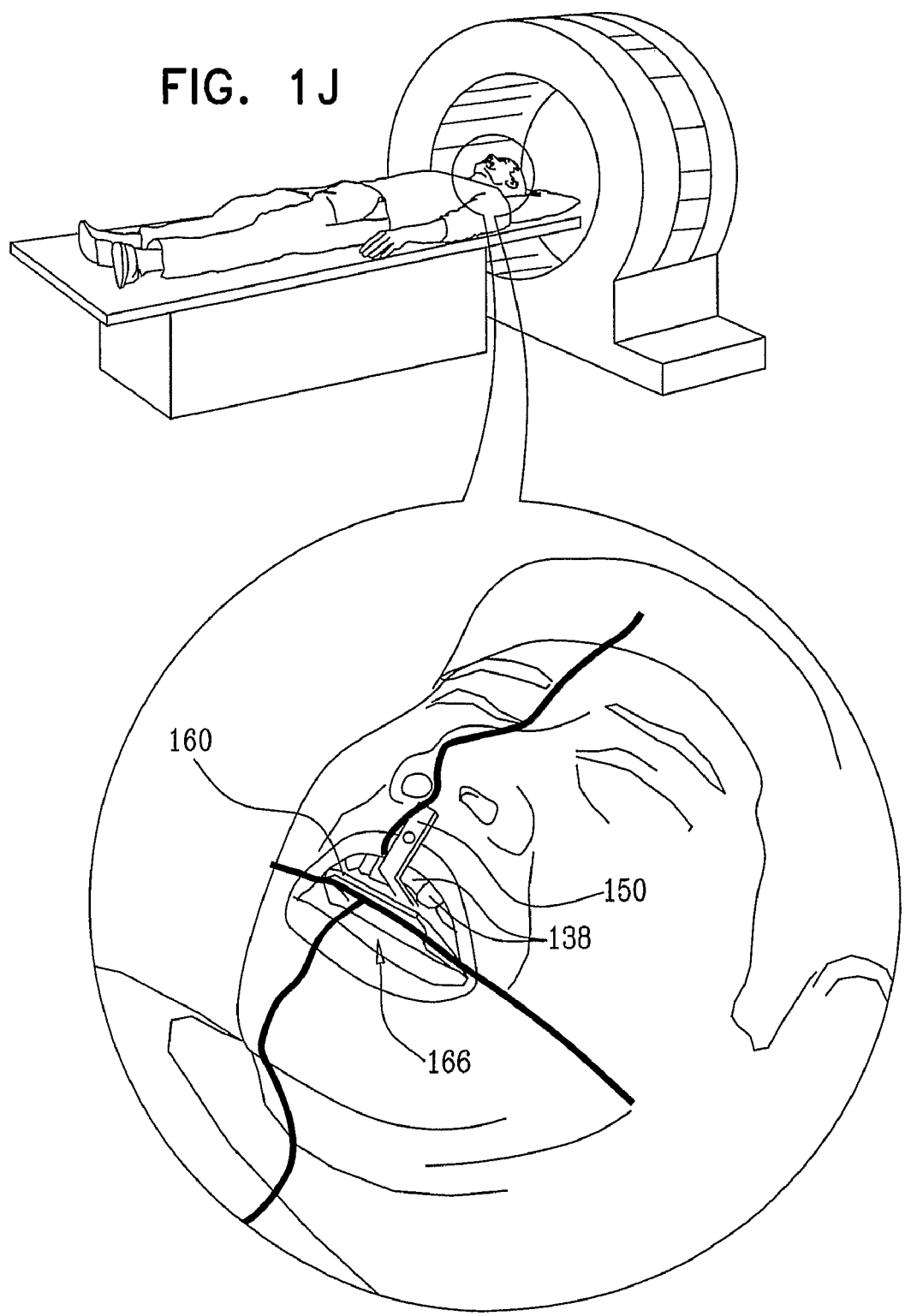

FIG. 1J shows the patient, having the assembly 166, including adhesively adhered mounting portion 150, carrier portion 160 and radio-opaque artificial teeth 138 being snap fitted onto spherical heads 104 of bone screws 100, inserted in the patient's mouth, undergoing CT imaging.

Figure 1K:
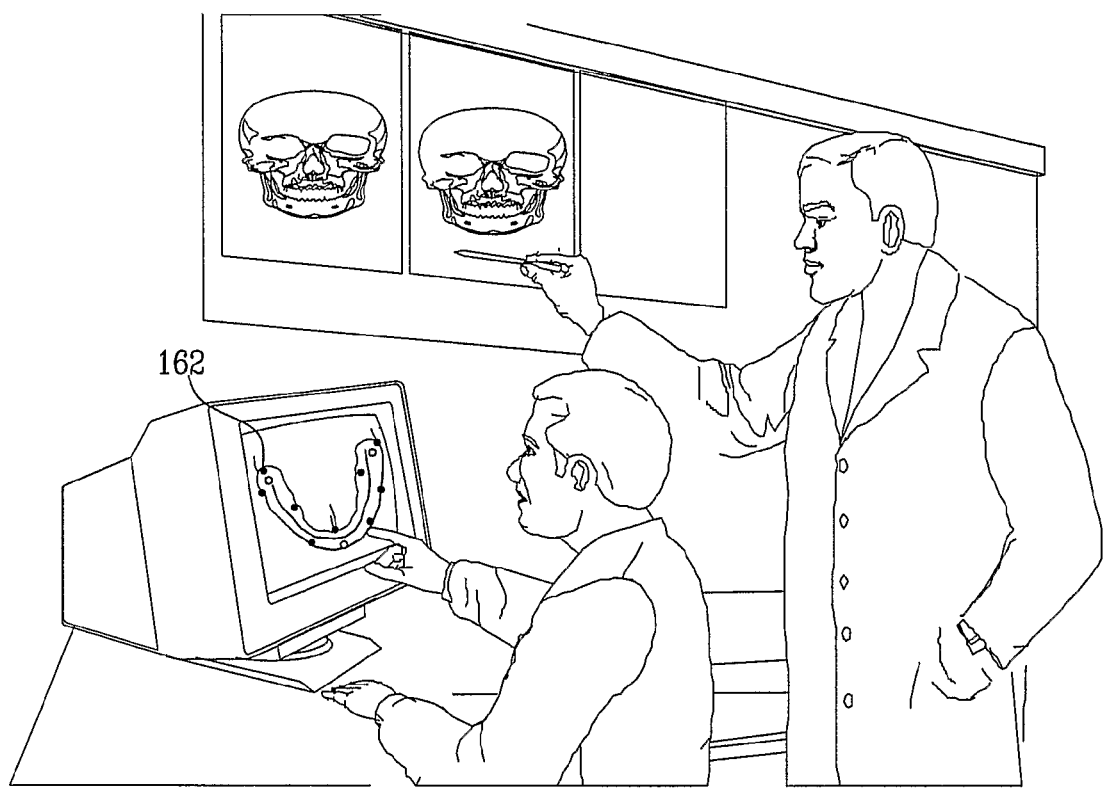

FIG. 1K illustrates an image produced by the CT imaging of FIG. 1J, being employed by a dental surgeon in computerized planning of an implant procedure. The resulting CT images establish three-dimensional spatial registration between the fiducial markers 162 and the patient's jaw.

FIG. 1L illustrates attachment of a patient tracking device 170 to the adhesively adhered mounting portion 150, carrier portion 160 and radio-opaque artificial teeth 138. Patient tracking device 170 is preferably a patient tracker, commercially available from Denx Ltd. under catalog number AIG 3302, and is mounted onto tracking device mounting rod 158. The patient tracking device 170 preferably includes a plurality of IR emitters 172, typically seven in number.

Three-dimensional spatial registration is then established between the IR emitters 172 of tracking device 170 and the fiducial markers 162 on carrier 160. This is preferably done by employing a conventional IR trackable handpiece 180, commercially available from Denx Ltd. under catalog number AIG 2400, and is described in applicant/assignee's published PCT application No. WO02/096261, which includes a multiplicity of IR emitters 182, typically 14 in number, and a three-dimensional IR imager 184, such as a tracking camera which is commercially available from Denx Ltd. under catalog number ATR0014.

Typically, as shown in FIG. 1L, an operator places a tip of a contact bit 186 mounted in handpiece 180, onto each fiducial marker 162 and images the three dimensional spatial relationship between that IR emitters 172 of the tracking device 170 and the IR emitters 182 of the handpiece 180, thus establishing the three-dimensional spatial relationship between that fiducial marker 162 and IR emitters 172 of the tracking device 170. This process is carried out sequentially for each of the fiducial markers 162, thus establishing the fixed three-dimensional spatial relationship between the patient tracking device 170 and the patient's jaw.

Figure 1M:
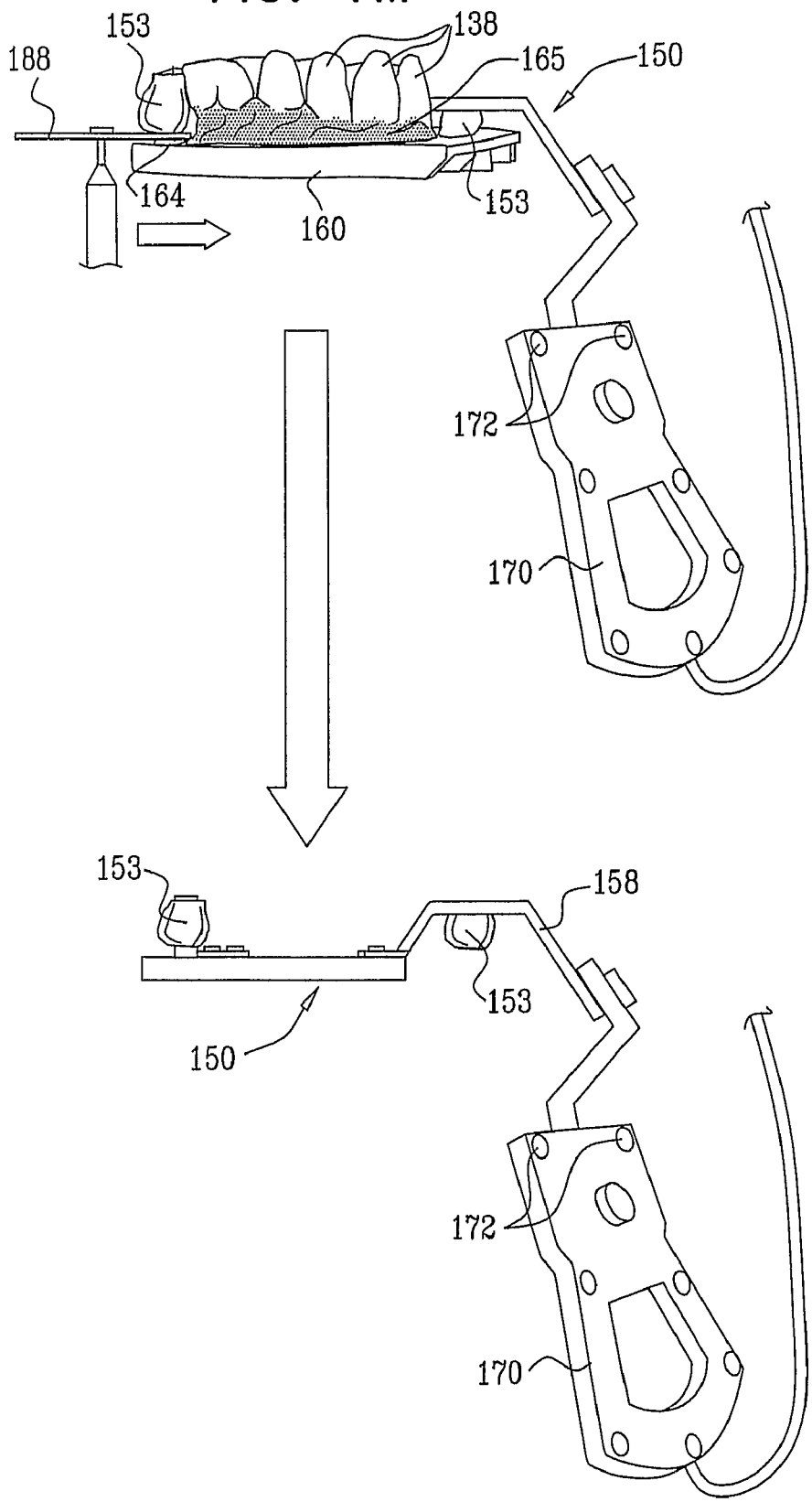

Reference is now made to FIG. 1M, which shows separating the fiducial carrier 160 and artificial radio-opaque teeth 138 adhered thereto from mounting portion 150. This is carried out by cutting the adhesive 164, as with a cutting disk 188.

Figure 1N:
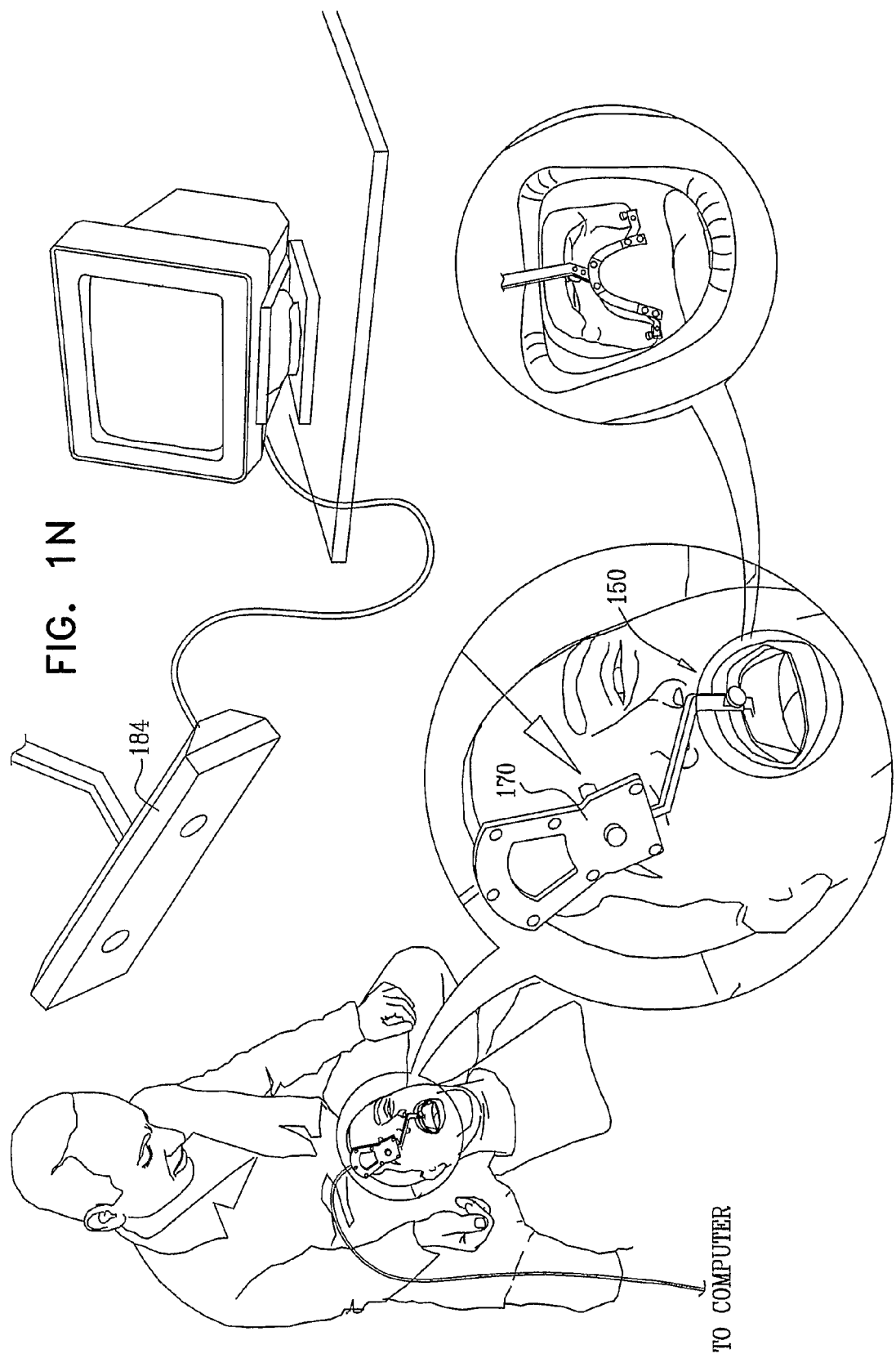
Figure 10:
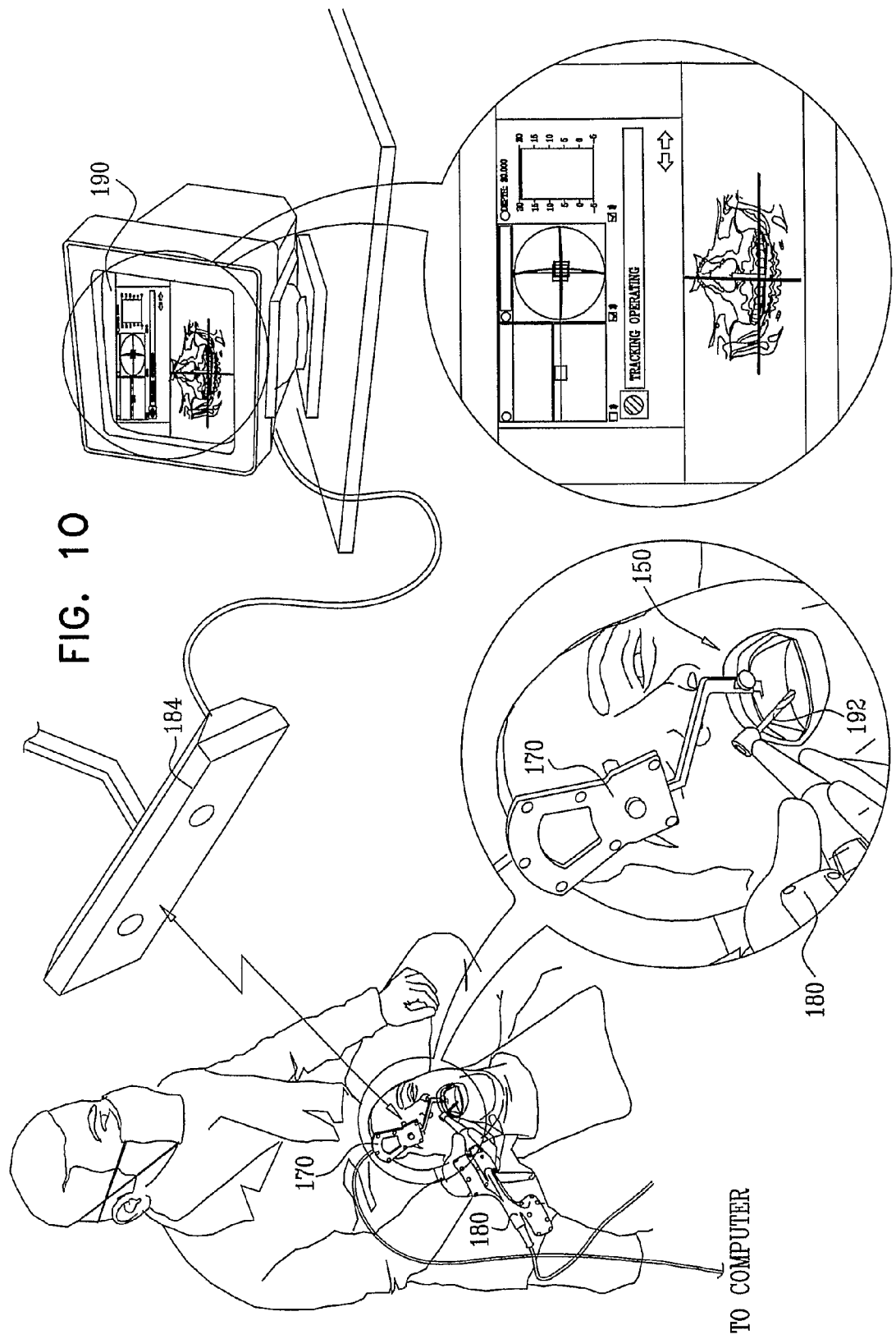

Referring now to FIG. 1N, it is seen that the mounting portion 150 which is fixedly coupled to the patient tracking device 170, is placed in the patient's mouth, preferably by snap-fitting retentive caps 144 (FIG. 1F) onto spherical heads 104 (FIG. 1A) of bone screws 100.

Reference is now made to FIG. 1O, which illustrates implant surgery carried out in accordance with a preferred embodiment of the present invention wherein the surgeon is guided by a display 190 which shows, in real time, the location of a drill bit 192 mounted onto handpiece 180 in relationship to the patient's jaw overlaid on a planned drilling trajectory, which is preferably prepared during an implant planning stage described hereinabove with reference to FIG. 1K.

Reference is now made FIGS. 2A, 2B, 2C, 2D, 2E, 2F, 2G, 2H, 2I and 2J, which are simplified pictorial illustrations of various stages in a method of placing an implant on a partially edentulous patient in accordance with another preferred embodiment of the present invention.

FIGS. 2A-2J describe a method for placing a tooth implant in a patient comprising the steps of attaching at least one attachment element to a patient's teeth by exclusively chairside configuring of at least a portion of the at least one attachment element to match the patient's teeth, mounting a carrier bearing at least one fiducial marker onto the attachment element, employing the carrier for providing registration between the at least one fiducial marker and the patient's jaw bone and placing the tooth implant by employing a tracking system which uses the registration to guide a drilling assembly.

Additionally in accordance with a preferred embodiment of the present invention, FIGS. 2A-2J describe a method for placing a tooth implant in a patient comprising the steps of exclusively chair-side attaching at least one radio-opaque tooth shape representation element to a patient's jaw, mounting a carrier bearing at least one fiducial marker onto the patient's jaw, employing the carrier and the at least one radio-opaque tooth shape representation element for providing registration between the at least one fiducial marker, the at least one radio-opaque tooth shape representation element and the patient's jaw bone and implanting the tooth implant by employing a tracking system which uses the registration to guide a drilling assembly.

Figure 2A:
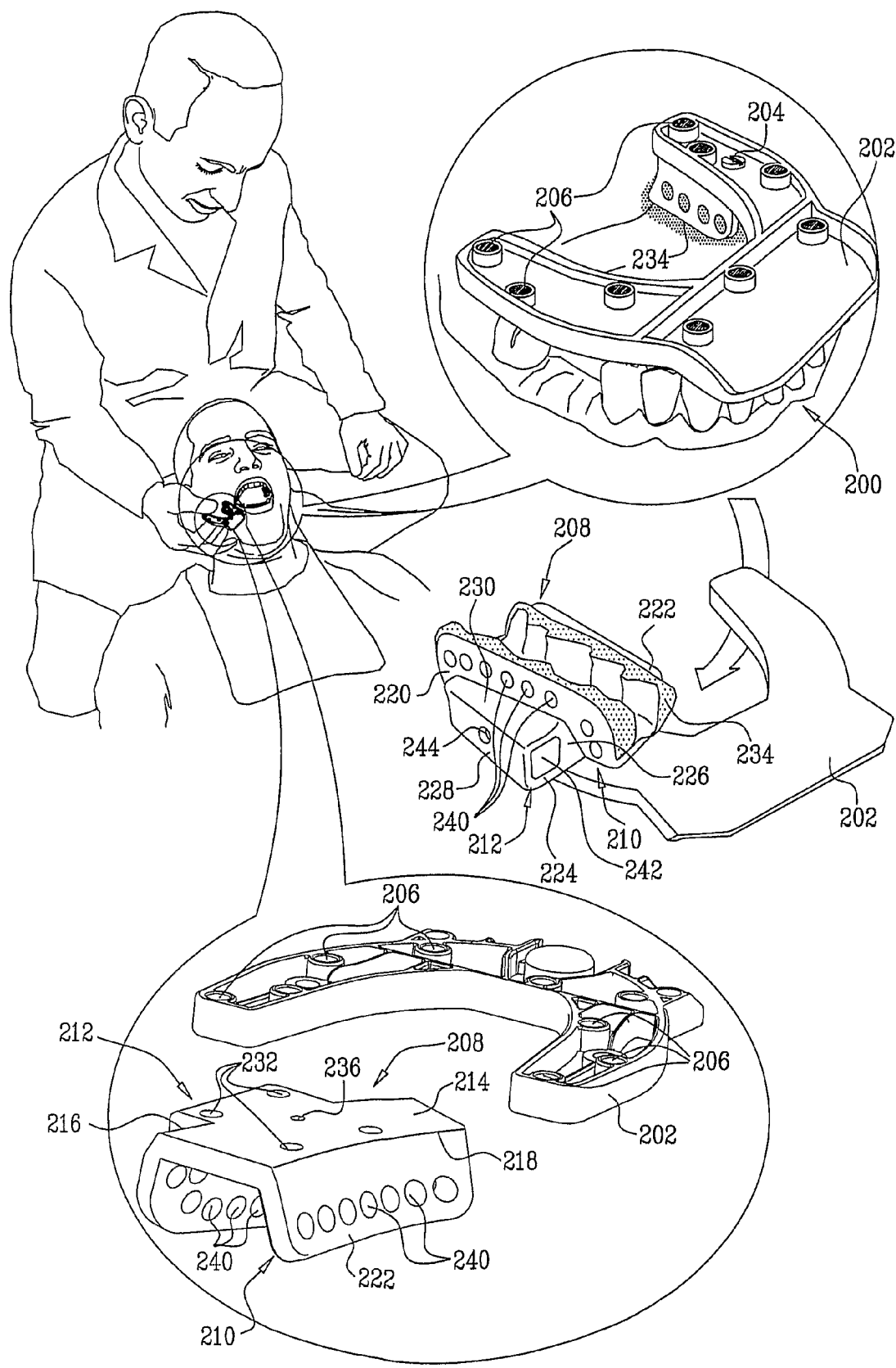

Referring now specifically to FIG. 2A, it is seen that a dentist is preparing a multipurpose tooth engagement assembly 200 which is seen to be associated with a fiducial carrier 202, preferably being attached thereto by a screw 204. Fiducial carrier 202 is commercially available from Denx Ltd. of Jerusalem, Israel, under catalog number AIG 3110. A plurality of fiducial markers 206, preferably nine in number and in the form of a ceramic sphere having a diameter of 3 mm are mounted on the carrier 202 at precise locations thereat.

Multipurpose tooth engagement assembly 200 preferably includes a multipurpose tooth engagement element 208, which preferably comprises a trough-like portion 210 which preferably is integrally formed with a channel-defining portion 212 lying alongside the trough-like portion 210. The trough-like portion 210 preferably includes a base 214 which has a generally straight edge 216 and a somewhat curved edge 218. Extending in a plane which is inclined outwardly with respect to base 214 along generally straight edge 216 is a first, generally straight, trough wall 220, which lies adjacent channel-defining portion 212. Extending in a plane which is inclined outwardly with respect to base 214 along curved edge 218 is a curved trough wall 222. Trough wall 222 is of a height which is approximately one half of the height of straight trough wall 220.

Channel defining portion 212 preferably includes a base 224 which is coplanar with base 214, an inner side wall 226 which is at least partially common with trough wall 220, an outer side wall 228 and a wall 230, which is generally parallel to and spaced from base 224.

Formed in base 214 are a plurality of recesses 232 for retaining impression material 234, which is preferably Z100 restorative, commercially available from 3M, and a threaded aperture 236 which accommodates screw 204. Trough walls 220 and 222 are preferably formed with a plurality of apertures 240.

Base 224 and walls 226, 228 and 230 of channel defining portion 212 together define a channel 242 which is configured to accept a mounting rod of a patient tracking device, as described hereinbelow with reference to FIG. 2H. An aperture 244 is preferably formed in wall 228 and communicates with channel 242 for accommodating a securing screw which threadably engages the mounting rod, as described hereinbelow with reference to FIG. 2H.

It is appreciated that various types and configurations of multipurpose tooth engagement elements and assemblies may be provided to conform to various regions of a patient's jaws.

It is seen that an impression is taken of part of the patient's teeth, using impression material 234, at a region preferably as far as possible from an intended implantation site. The impression material 234 is hardened while on the patient's teeth, preferably by light curing. It is appreciated that since the impression material 234 is hardened and it is sought to be able to repeatedly remove and replace the impression onto the patient's teeth with a high level of accuracy, care must be taken to prevent the impression material from entering interstices of the patient's teeth, as by blocking with a suitable filler material (not shown), such as ORASEAL® putty, commercially available from Ultradent Products Inc. of Jordan, Utah USA. Alternatively, should the impression material have entered undercuts or interstices of the patient's teeth, those portions of the impression may be excised by cutting using conventional dental tools.

Figure 2B:

Referring now to FIG. 2B, it is seen that following hardening of the impression the multipurpose tooth engagement assembly 200 and the associated fiducial carrier 202 are removed from the mouth of the patient and a conventional radiolucent impression material 246, such as IMPREGUM SE, commercially available from 3M, is applied to the intended implantation site.

Figure 2C:
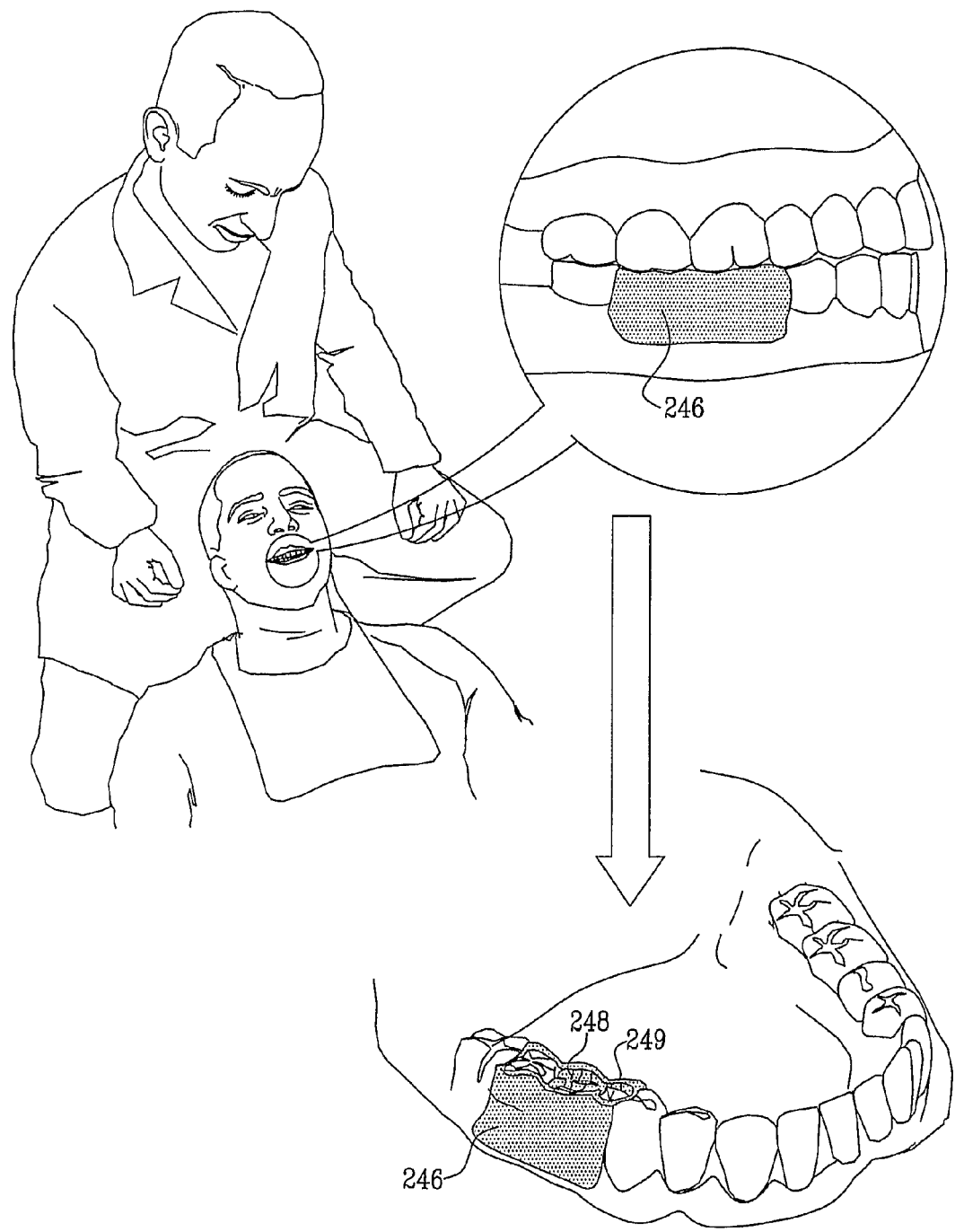

As seen in FIG. 2C, the patient is required to bite down on the impression material 246, prior to hardening thereof, thereby to impress on material 246 the shape of the antagonist teeth, as shown at reference numeral 248. The impression material 246 is allowed to harden to define a radiolucent impression 249, prior to the patient opening his mouth.

Figure 2D:
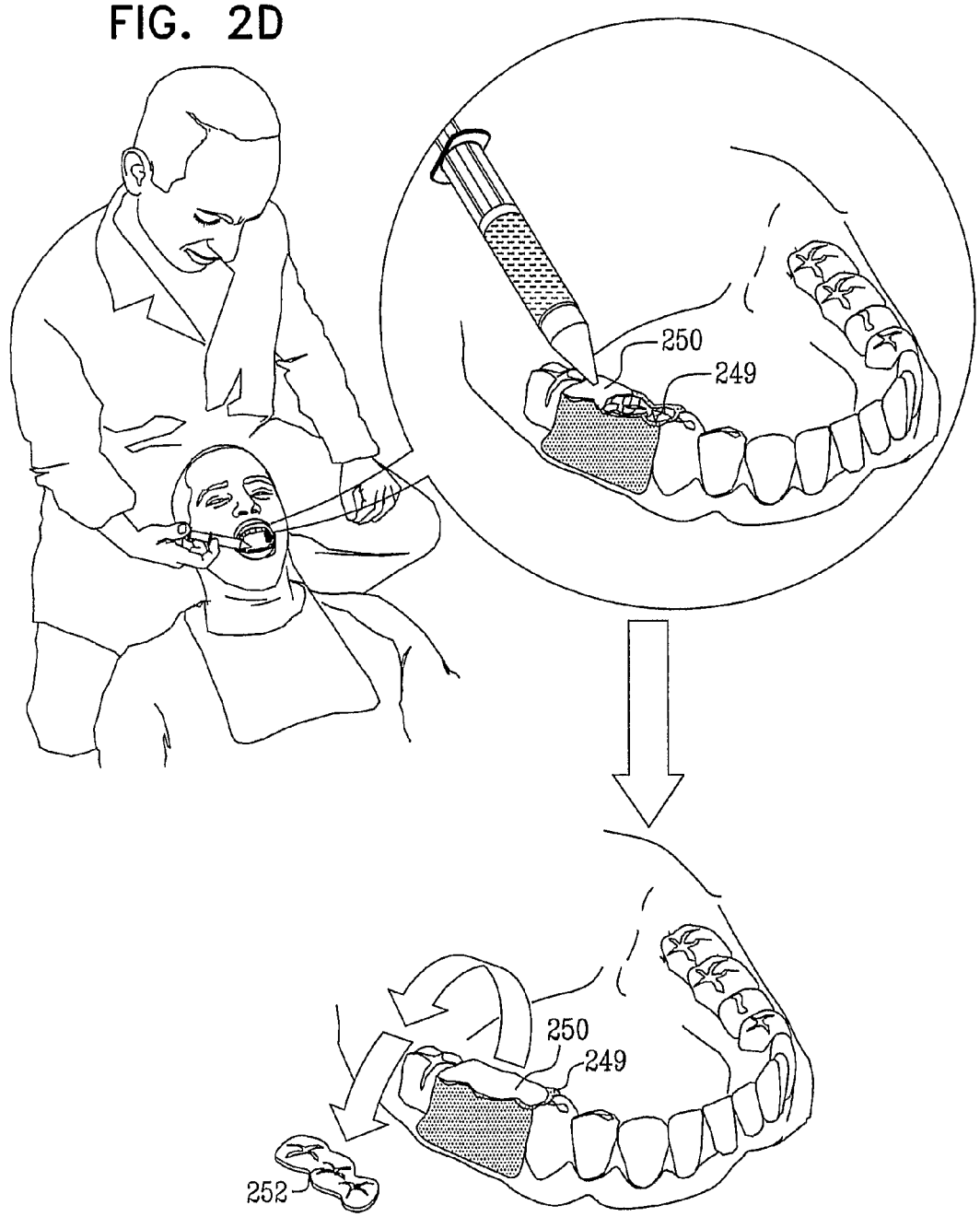

Reference is now made to FIG. 2D, which shows injection of a hardenable radio-opaque material 250, such as LUXATEMP® fluorescence, commercially available from Zenith/DMG of Englewood, N.J., USA, into the impression 249. The material 250 is allowed to harden, thus providing a radio-opaque model 252 of relevant surfaces of the antagonist teeth.

Figure 2E:
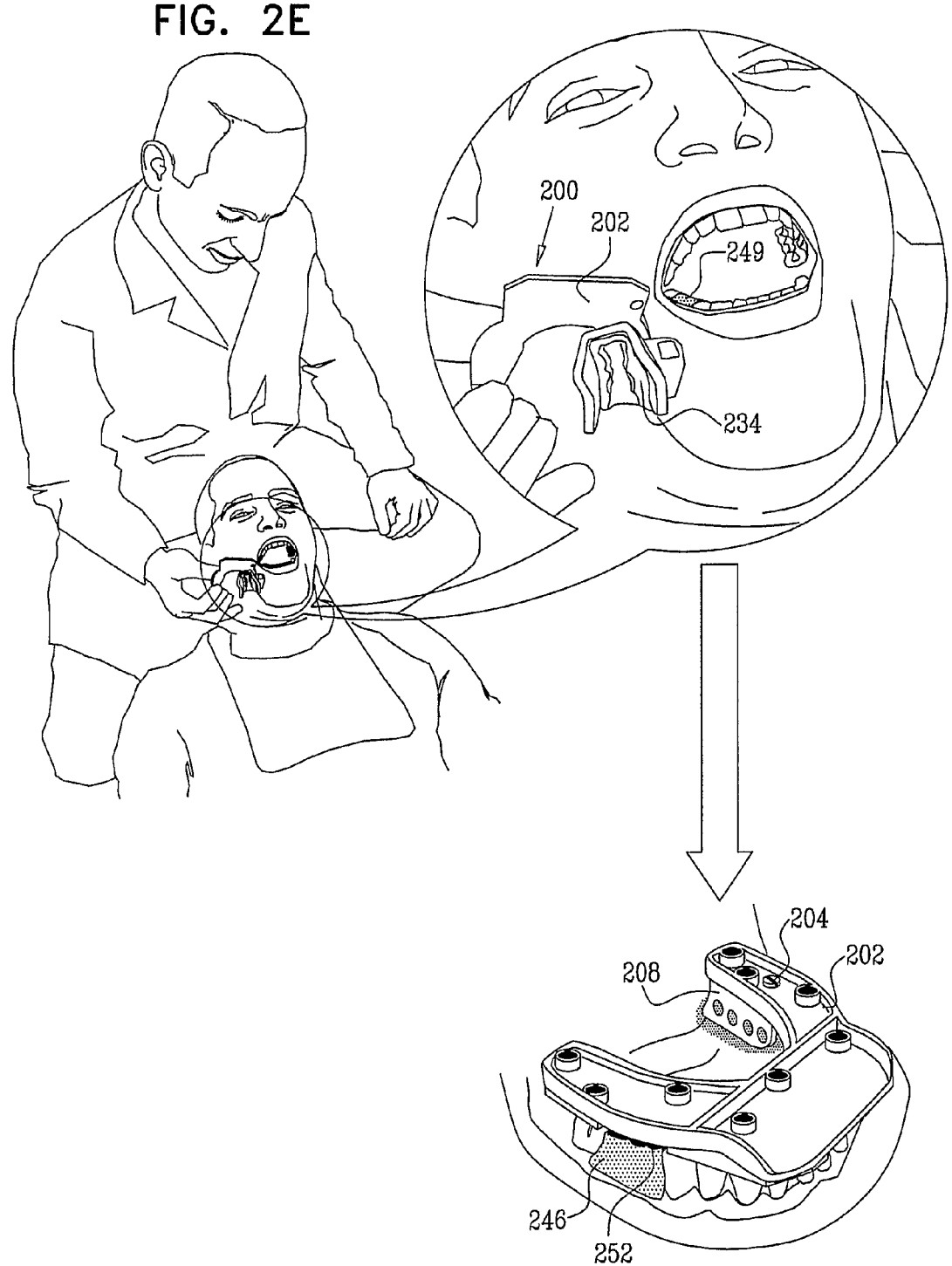

Referring now to FIG. 2E, it is seen that the multipurpose tooth engagement assembly 200 and the associated fiducial carrier 202 are returned to the mouth of the patient and precisely repositioned therein such that the fiducial carrier 202 overlies, inter alia, the radio-opaque model 252 and the impression 249.

Figure 2F:
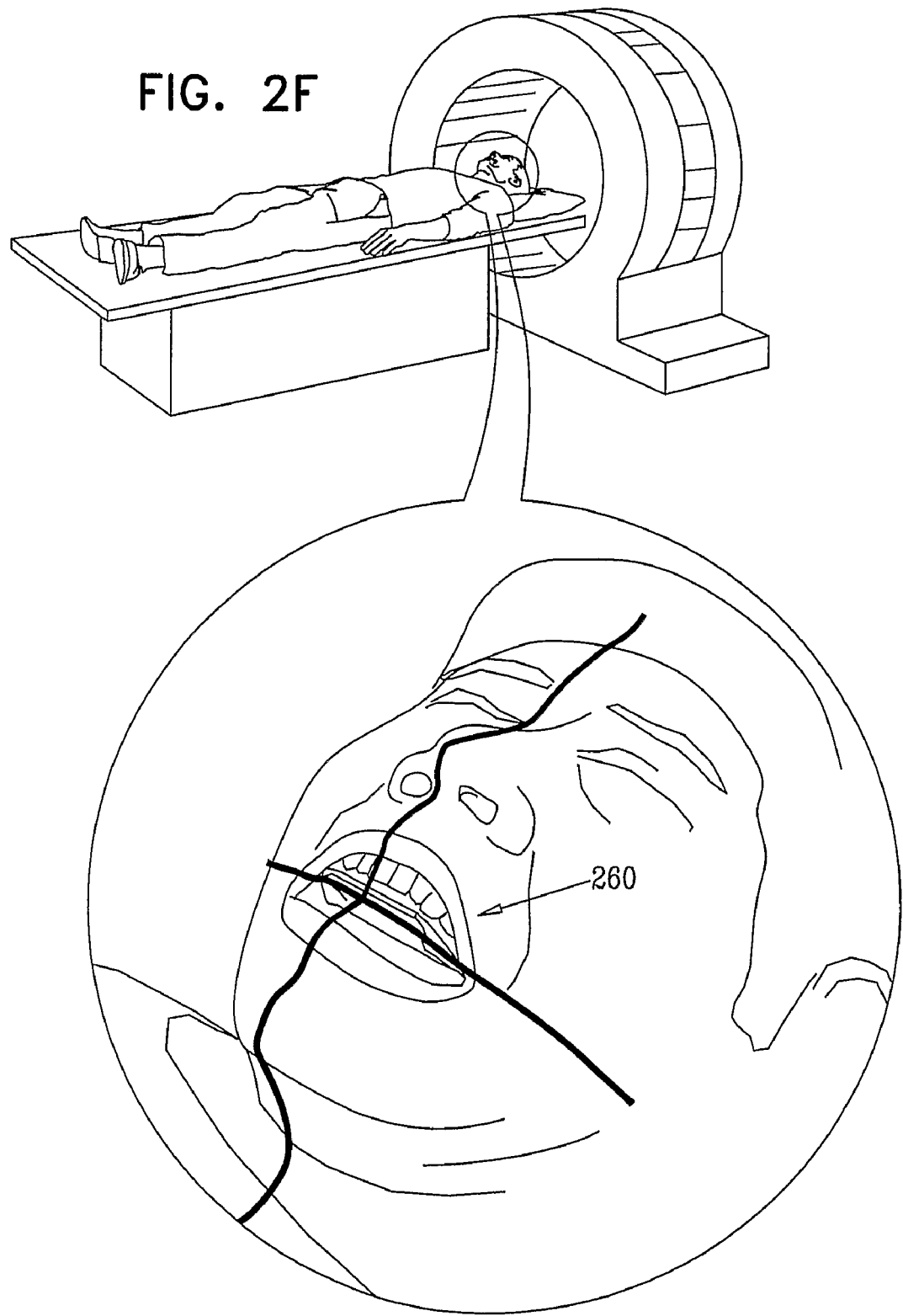

Reference is now made to FIG. 2F, which shows a CT imagable registration assembly 260, including the multipurpose tooth engagement assembly 200, the associated fiducial carrier 202, the radio-opaque model 252 and the radiolucent impression 249 inserted into a patient's mouth and secured therein by the patient tightly closing his jaws during CT imaging. Following CT imaging the assembly 260 is removed from the patient's mouth.

Figure 2G:
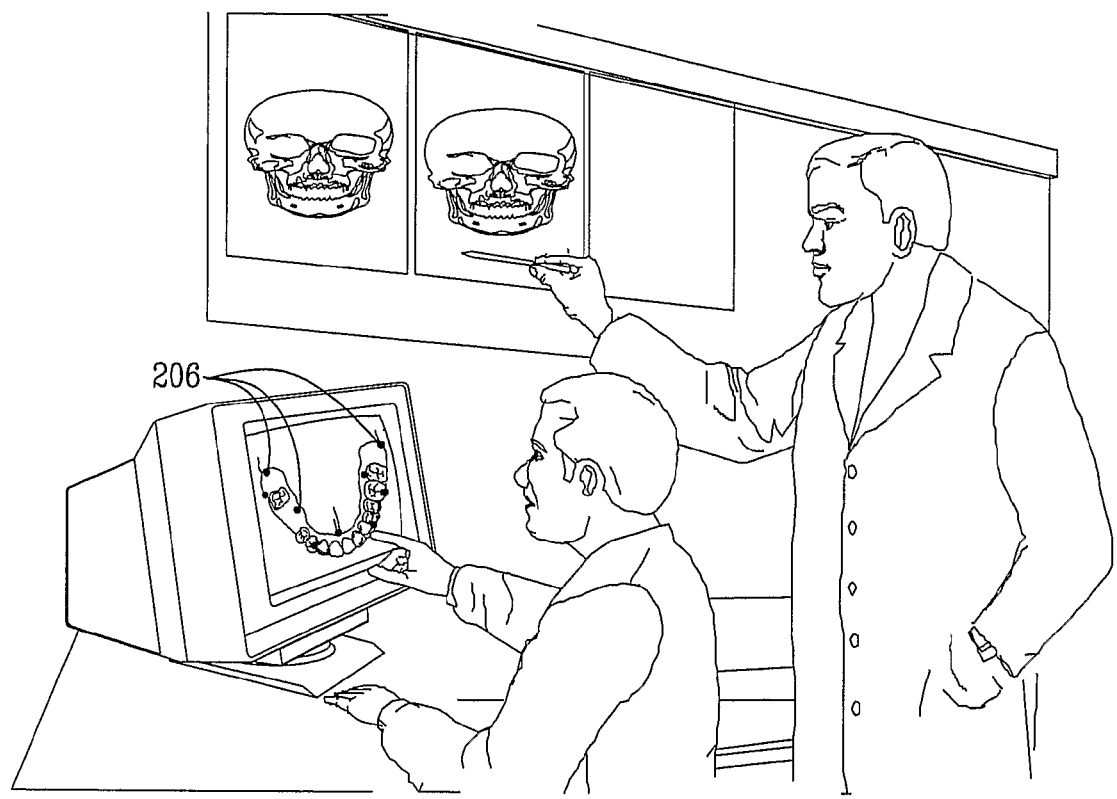

FIG. 2G illustrates an image produced by the CT imaging of FIG. 2F, being employed by a dental surgeon in computerized planning of an implant procedure. The resulting CT images establish three-dimensional spatial registration between the fiducial markers 206 and the patient's jaw.

Figure 2H:
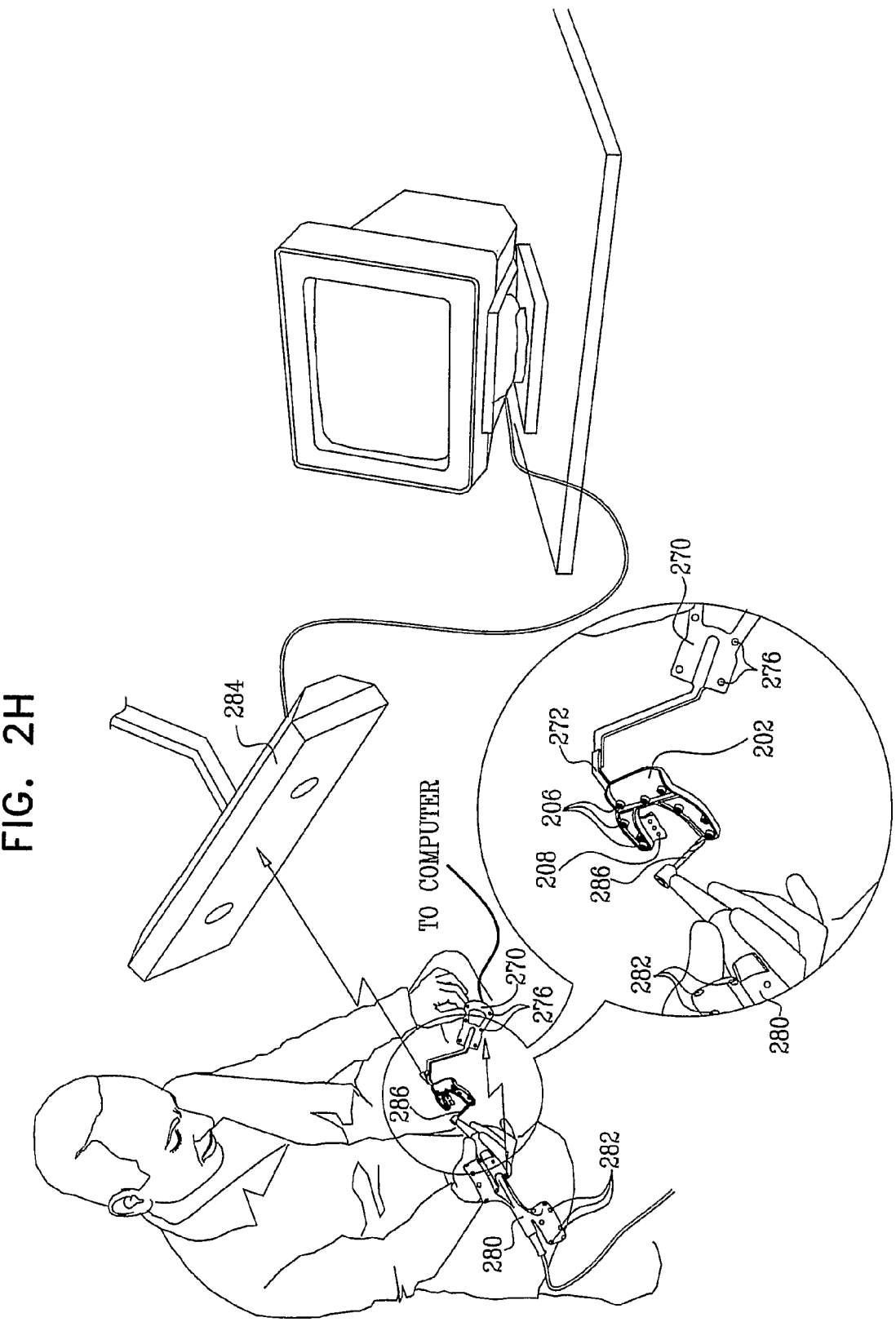
Figure 21:
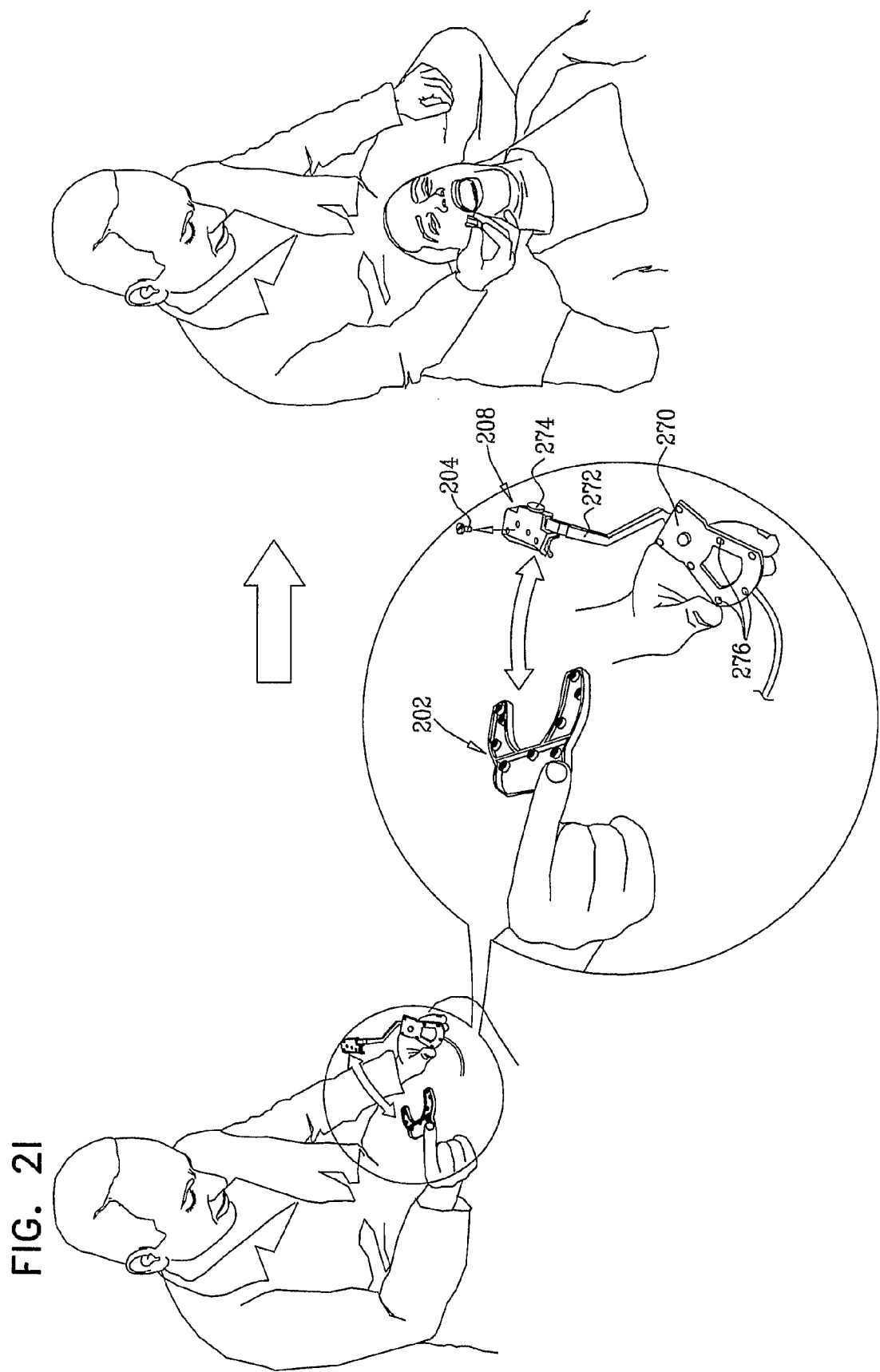

FIG. 2H illustrates attachment of a patient tracking device 270 to the multipurpose tooth engagement element 208 by inserting a rod 272 of device 270 into channel 242 and securing it by means of a securing screw (not shown), which extends through aperture 244. Patient tracking device 270 is preferably a patient tracker, commercially available from Denx Ltd. under catalog number AIG 3302. The patient tracking device 270 preferably includes a plurality of IR emitters 276, typically seven in number.

Three-dimensional spatial registration is then established between the IR emitters 276 of tracking device 270 and the fiducial markers 206 on carrier 202. This is preferably done by employing an IR trackable handpiece 280, commercially available from Denx Ltd. under catalog number AIG 2400, and is described in applicant/assignee's published PCT application No. WO02/096261, which includes a multiplicity of IR emitters 282, typically 14 in number, and a three-dimensional IR imager 284, such as a tracking camera which is commercially available from Denx Ltd. under catalog number ATR0014.

Typically, as shown, an operator places a tip of a contact bit 286 mounted in handpiece 280, onto each fiducial marker 206 and images the three dimensional spatial relationship between that IR emitters 276 of the tracking device 270 and the IR emitters 282 of the handpiece 280, thus establishing the three-dimensional spatial relationship between that fiducial marker 206 and IR emitters 276 of the tracking device 270. This process is carried out sequentially for each of the fiducial markers 206, thus establishing the fixed three-dimensional spatial relationship between the patient tracking device 270 and the patient's jaw.

Reference is now made to FIG. 2I, which illustrates separation of the multipurpose tooth engagement element 208 from fiducial carrier 202, as by removal of screw 204. The multipurpose tooth engagement element 208 is then adhesively and precisely mounted in the patient's mouth, preferably by use of conventional impression material 286, such as IMPREGUM SE applied to sides of the patient's teeth.

Reference is now made to FIG. 2J, which illustrates implant surgery carried out in accordance with a preferred embodiment of the present invention wherein the surgeon is guided by a display 290 which shows, in real time, the location of a drill bit 292 mounted onto handpiece 280 in relationship to the patient's jaw overlaid on a planned drilling trajectory, which is preferably prepared during an implant planning stage described hereinabove with reference to FIG. 2G.

It will be appreciated by persons skilled in the art that the present invention is not limited by what has been particularly shown and described hereinabove. Rather the scope of the present invention includes combinations and subcombinations of various features of the present invention as well as modifications which would occur to persons reading the foregoing description and which are not in the prior art.

The invention claimed is:

1. A method for implanting a tooth implant in an at least partially edentulous patient comprising the steps of:
   anchoring at least one attachment element in the at least partially edentulous patient's jaw bone;
   removably and replaceably mounting a carrier assembly bearing at least one fiducial marker onto said at least one attachment element in a precisely repeatable position with respect to said at least partially edentulous patient's jaw bone,
   the at least one attachment element comprising at least three jaw bone fasteners distributed at positions on a plane such that whenever the carrier assembly bearing the at least one fiducial marker is remounted onto said at least one attachment element, the carrier assembly is prevented from rotating outside of the plane and the at least one fiducial marker regains a same spatial position relative to the at least partially edentulous patient's jaw bone
   the carrier assembly thereby being removable and replaceable into the precisely repeatable position without having to remove the at least one attachment element from the at least partially edentulous patient's jaw bone,
   providing in the carrier assembly a carrier mount that has a mounting portion, the mounting portion configured to allow the carrier assembly to securely and removably connect to the at least three jaw bone fasteners without blocking the implanting of the tooth implant, the mounting portion connected to a tracking device external to the mouth of the patient, the mounting portion including a mounting element running parallel to the jaw bone of the at least partially edentulous patient;
   employing said carrier for providing registration between said at least one fiducial marker and said at least partially edentulous patient's jaw bone; and
   implanting said tooth implant in said at least partially edentulous patient by employing a tracking system which uses said registration to guide a drilling assembly.

2. A method for implanting a tooth implant according to claim 1 and wherein said at least one attachment element comprises at least three jaw bone fasteners including one at a midline of the jaw and one each at posterior ends of the jaw of the at least partially edentulous patient.

3. A method for implanting a tooth implant according to claim 2 wherein each of said at least three jaw bone fasteners has a generally ball-shaped head.

4. A method for implanting a tooth implant according to claim 1 and also comprising, following said anchoring and prior to said removably and replaceably mounting a carrier assembly: removably and replaceably mounting at least one intermediate element on said at least one attachment element; taking an impression of said patient's jaw; employing said impression of said patient's jaw to provide a model of said patient's jaw; mounting at least one carrier mount onto said at least one intermediate element; and mounting a fiducial carrier bearing said at least one fiducial marker onto said at least one carrier mount, thereby to provide said carrier assembly.

5. A method for implanting a tooth implant according to claim 4, and wherein said removably and replaceably mounting at least one intermediate element comprises removably and replaceably mounting at least one impression cap having a flat surface onto said at least one attachment element.

6. A method for implanting a tooth implant according claim 4 and also comprising, prior to said anchoring:
   taking a preliminary impression of said patient's jaw; and
   employing said preliminary impression for preparing a temporary base and rim suited to said patient's jaw.

7. A method for implanting a tooth implant according to claim 4 and wherein said employing said impression of said patient's jaw to provide a model comprises:
   employing said impression to provide a model, which has anchored therein at least one attachment element analog;
   removeably positioning radio-opaque artificial teeth on said model.

8. A method for implanting a tooth implant according to claim 7 and wherein said mounting at least one carrier mount onto said at least one intermediate element comprises adhering said at least one carrier mount to said at feast one intermediate element, while said at least one intermediate element is mounted onto said at least one attachment element analog.

9. A method for implanting a tooth implant according to claim 7 and wherein said removably and replaceably mounting a carrier assembly comprises removably and replaceably mounting said at least one intermediate element, said at least one carrier mount, said radio-opaque artificial teeth and said fiducial carrier onto said at least one attachment element in a precisely repeatable position with respect to said patient's jaw bone.

10. A method for implanting a tooth implant according to claim 1 and wherein:
    said employing said carrier assembly for providing registration comprises providing at least one CT image of said patient's jaw while said carrier assembly is mounted onto said at least one attachment element; and
    the method also comprises, prior to said implanting said tooth implant, providing three-dimensional registration between said at least one fiducial marker, said tracking system and said drilling assembly.

11. The method of claim 1, further comprising the mounting portion cooperating with an engagement portion, the mounting element having a plurality of connection positions for connection to the engagement portion, the engagement portion configured to connect the mounting element to the at least three jaw bone fasteners.

12. The method of claim 11, further comprising the mounting portion including a tracking device mounting rod configured to extend outside of the mouth of the patient and connect to the tracking device.

13. The method of claim 11, further comprising the engagement portion configured to connect the mounting element to each of at least three of the at least three jaw bone fasteners.

14. The method of claim 1, further comprising providing the drilling assembly with a handpiece that has emitters configured in two groups such that the emitters are visible by a tracking camera even if the handpiece is rotated on one of (i) its axis and (ii) an axis of a drill bit of the handpiece, during the implanting.

15. The method of claim 14, further comprising positioning one group of emitters on a first element projecting from a side of the handpiece and positioning a second group of emitters on a second element projecting from an opposite side of the handpiece.

16. The method of claim 15, further comprising having the first and second elements curve radially around an axis of movement of the handpiece.

17. The method of claim 1, further comprising a display displaying a location of a drill bit of the drilling assembly in relationship to the at least partially edentulous patient's jawbone, the displaying of the location being overlaid on a planned drilling trajectory.

18. The method of claim 17, further comprising the display displaying several indicators including a depth indicator that indicates the depth of the drill bit.

19. Apparatus for use in implanting a tooth implant comprising:
- at least one attachment element including an anchor portion configured for anchoring in an at least partially edentulous patient's jaw bone and an attachment portion, the at least one attachment element comprising at least three jaw bone fasteners distributed at positions on a plane such that whenever the carrier assembly bearing the at least one fiducial marker is remounted onto said at least one attachment element, the carrier assembly is prevented from rotating outside of the plane and the at least one fiducial marker regains a same spatial position relative to the at least partially edentulous patient's jaw bone; and
- a fiducial marker carrier assembly containing a plurality of fiducial markers and including at least one mounting portion configured for removable and replaceable mounting onto said attachment portion of said at least one attachment element in a precisely repeatable position with respect to the at least partially edentulous patient's jaw bone, the fiducial marker carrier assembly configured to be removable and replaceable into the precisely repeatable position without having to remove the at least one attachment element from the at least partially edentulous patient's jaw bone
- the mounting portion including a mounting element running parallel to the jaw bone of the at least partially edentulous patient and configured to allow the carrier assembly to securely and removably connect to the at least three jaw bone fasteners without blocking the implanting of the tooth implant.

20. Apparatus for use in implanting a tooth implant according to claim 19 and wherein: said at least one attachment element said at least one jaw bone fastener comprises three jaw bone fasteners, each having a generally ball-shaped head; and said at least one mounting portion includes three mounting portions, each configured for removable and replaceable mounting onto said attachment portion of one of said three jaw bone fasteners in a precisely repeatable position with respect to said patient's jaw bone.

21. Apparatus for use in implanting a tooth implant according to claim 19 and also comprising: at least one intermediate element configured to be mounted onto said attachment portion of said at least one attachment element and to have said fiducial marker carrier assembly mounted thereon; at least one carrier mount configured to be mounted onto said at least one intermediate element; and a fiducial carrier bearing said plurality of fiducial marker configured to be mounted onto said at least one carrier mount, thereby to provide said fiducial marker carrier assembly.

22. Apparatus for use in implanting a tooth implant according to claim 21 and wherein said fiducial marker carrier assembly comprises said at least one intermediate element, said at least one carrier mount, said fiducial carrier and a plurality of radio-opaque artificial teeth.

23. Apparatus for use in implanting a tooth implant according to claim 22 and wherein said fiducial marker carrier assembly comprises a first adhesive adhering said fiducial carrier to said at least one carrier mount and a second adhesive adhering said radio-opaque artificial teeth to said fiducial carrier.

24. Apparatus for use in implanting a tooth implant according to claim 19 and also comprising a tracking system including at least one IR emitter configured for providing tracking of motions of said patient during implantation of said tooth implant.

25. Apparatus for use in implanting a tooth implant according to claim 19 and also comprising a dental surgery device including at least one IR emitter configured for providing tracking of motions of a dental surgeon during implantation of said tooth implant.

26. The apparatus of claim 19, wherein said at least one attachment element comprises at least three jaw bone fasteners including one at a midline of the jaw and one each at posterior ends of the jaw of the at least partially edentulous patient.

27. The apparatus of claim 19, further comprising the mounting portion further including an engagement portion, the mounting element having a plurality of connection positions for connection to the engagement portion, the engagement portion configured to connect the mounting element to the at least three jaw bone fasteners.

28. The apparatus of claim 27, further comprising the engagement portion configured to connect the mounting element to each of at least three of the at least three jaw bone fasteners.

29. The apparatus of claim 27, further comprising the mounting portion including a tracking device mounting rod configured to extend outside of the mouth of the patient and connect to the tracking device.

30. The apparatus of claim 19, further comprising the drilling assembly having a handpiece that has emitters, one group of emitters on a first element projecting from a side of handpiece and a second group of emitters on a second element projecting from an opposite side of the handpiece.

31. The apparatus of claim 30, further comprising having the first and second elements curve radially around one of (i) an axis of the handpiece and (ii) an axis of a drill bit of the handpiece, such that the emitters are visible by a tracking camera upon rotation of the handpiece on the axis.

32. The apparatus of claim 19, further comprising a display displaying a location of a drill bit of the drilling assembly in relationship to the at least partially edentulous patient's jawbone, the location overlaid on a planned drilling trajectory.

33. The method of claim 32, further comprising the display displaying several indicators including a depth indicator that indicates the depth of the drill bit.

* * * * *